United States Patent [19]

Kamiya et al.

[11] 4,264,498
[45] Apr. 28, 1981

[54] PROCESS FOR THE PREPARATION OF 1,3-DISUBSTITUTED-2-AZETIDINONES FROM TRIAZINES

[75] Inventors: Takashi Kamiya, Suita; Masashi Hashimoto, Takarazuka; Osamu Nakaguti, Toyonaka; Teruo Oku, Osaka; Yoshiharu Nakai, Otsu; Hidekazu Takeno, Nara, all of Japan

[73] Assignee: Fujisawa Pharmaceutical Co., Ltd., Osaka, Japan

[21] Appl. No.: 13,399

[22] Filed: Feb. 21, 1979

Related U.S. Application Data

[63] Continuation-in-part of Ser. No. 756,986, Jan. 5, 1977, abandoned.

[30] Foreign Application Priority Data

Jan. 5, 1976 [GB] United Kingdom ............... 24275/76

[51] Int. Cl.³ ................. C07D 205/08; C07D 201/02; C07D 403/04; A67K 31/395
[52] U.S. Cl. ............................... 260/239 A; 544/193; 544/215; 549/59; 260/245.4; 424/244
[58] Field of Search ..................... 260/239 A

[56] References Cited

U.S. PATENT DOCUMENTS 3,943,123   3/1976   Bose ................................. 260/239 A

OTHER PUBLICATIONS

Ziegler et al., Monat. 99, 2128–2133, (1968).
Mukeyee et al., Synthesis 1973, 334–337.
Smolin et al., "S–triazines and Derivatives", (1959), pp. 493, 494.
Kamiya et al., Chem. Abs. 85, 21078b, (1976).

Primary Examiner—Mark L. Berch
Attorney, Agent, or Firm—Dayton R. Stemple, Jr.

[57] ABSTRACT

A process for preparing an azetidinone of the formula:

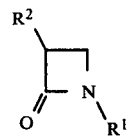

which comprises reacting a C-unsubstituted methyleneamine of the formula:

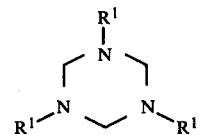

with $R^2$—$CH_2COOH$, its acid halide or anhydride, in the presence of boron trihalide and an organic base, wherein $R^1$ is an organic residue bearing a carboxy group or its derivative and $R^2$ is azido, substituted amino, halogen, acyloxy, alkoxy, aryloxy or aralkoxy.

4 Claims, No Drawings

PROCESS FOR THE PREPARATION OF 1,3-DISUBSTITUTED-2-AZETIDINONES FROM TRIAZINES

This invention is a continuation-in-part application of co-pending application Ser. No. 756,986, filed on Jan. 5th, 1977, now abandoned.

This invention is based on success of identification of the chemical structure of FR-1923 substance called as Nocardicin A. That is, FR-1923 substance (Nocardicin A) is a known antibiotic selected from the fermentation broth of a strain of the genus, Nocardia, particularly *Nocardia uniformis* subsp. *tsuyamanensis* (ATCC No. 21806) and now identified as the following chemical structure.

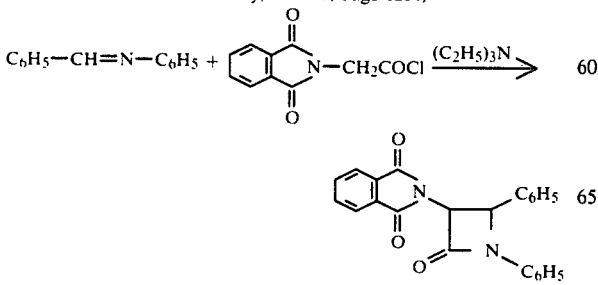

This identification of chemical structure of the above attractive and unique monocyclic β-lactam antibiotic, FR-1923 substance encouraged the inventors of this invention to study on the synthesis for preparing 1,3-disubstituted-2-azetidinone of the formula:

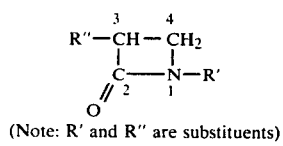

(Note: R' and R" are substituents)

As to synthesis methods of the monocyclic β-lactam compounds, there have been many reports for preparation of 1,3,4-trisubstituted-2-azetidinone from C,N-disubstituted methyleneamine compound and either of substituted acetic acid or ketene compound which is equivalent to said substituted acetic acid as shown in the following.

(1) E. Ziegler, Th. Wimmer and Heidrun Mittelbach. (Monatschefte fur Chemie, Vol. 99, Page 2128-2138)

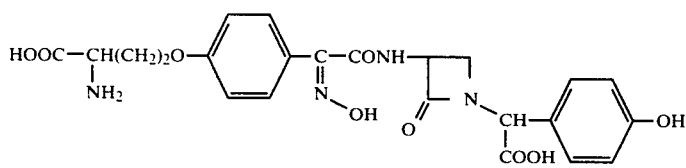

(2) John C. Sheehan and James J. Ryan. (Journal of the American Chemical Society, Vol. 73, Page 1204)

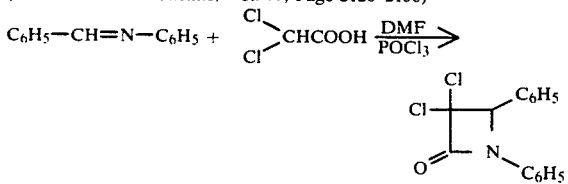

(3) Ajay K. Bose. (USP 3,943,123)

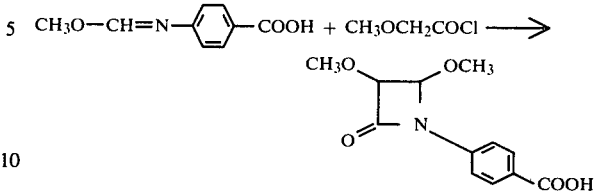

(4) R. Pfleger and A. Jager (Chemishe Berichte, Vol. 90, Page 2460)

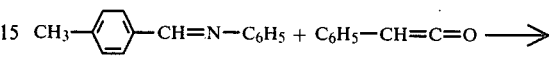

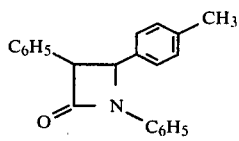

On the other hand, it is known that a trimer of C-unsubstituted methyleneamine compound, i.e.: $[CH_2=N-R']_3$ (note: R' is substituent) is once transformed into its monomer in the presence of a weak acid of hydrogen cyanide, phenol and sodium bisulfite to give only an adduct thereof with said acid as shown in the following.

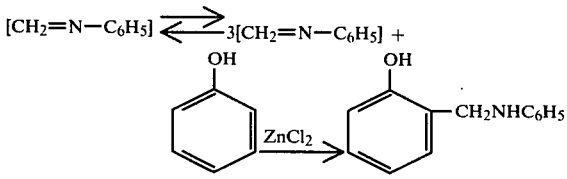

On the basis of such prior technical information, some trials for preparation of 1,3-disubstituted-2-azetidinone from C-unsubstituted methyleneamine compound and ketene compound, which is equivalent to the aforementioned substituted acetic acid were also carried out, but such trials have not been successful, the fact of which is shown in the following.

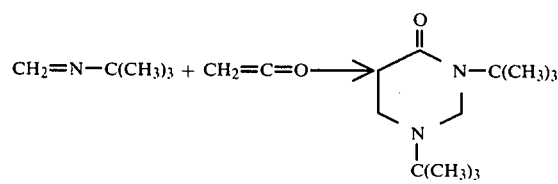

Under such a state of the prior art, the synthesis of 1,3-disubstituted-2-azetidinone from C-unsubstituted methyleneamine was neither anticipated nor obvious to a person skilled in the arts.

Nevertheless, as the result of extensive study, the inventors of this invention firstly have succeeded in synthesizing said 1,3-disubstituted-2-azetidinone from a trimer of C-unsubstituted methyleneamine compound in the presence of boron trihalide and a base by a single step.

This new synthesis method is characterized by using boron trihalide and is new, unique and industrial synthesis for preparing 1,3-disubstituted-2-azetidinone.

The present invention is concerned with a new and unique process for the preparation of 1,3-disubstituted-2-azetidinone. More particularly, it is concerned with a process for the preparation of 1,3-disubstituted-2-azetidinone (III) which comprises reacting methyleneamine compound (I) with substituted acetic acid (II) or its reactive derivative of the carboxy function in the presence of a Lewis acid and a base.

The present invention provides a new process for preparing 1,3-disubstituted-2-azetidinone in higher yield by one step synthesis.

Accordingly, the present invention provides a novel and simple process for the industrial manufacture of 1,3-disubstituted-2-azetidinone, which gives high yield.

The object compounds (III) of the present invention include new compounds and known ones to the public in literature, e.g. German Offenlegungsschrift No. 25 29 941. The inventors of the present invention have made an extensive study of a synthetic process for the industrial manufacture of said compounds and succeeded in inventing a new, unique and industrial process for preparing 1,3-disubstituted-2-azetidinone (III).

The process of the present invention is represented by the following scheme for convenience' sake.

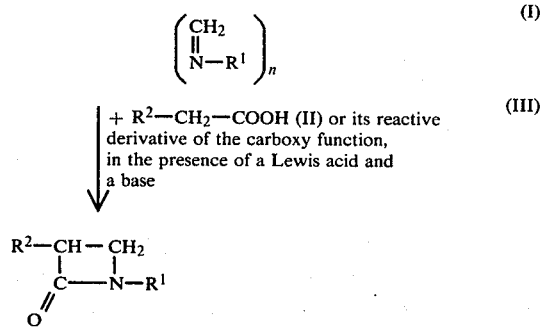

wherein $R^1$ is an organic residue bearing a carboxy group or its derivative,
n is an integer of one to three, and
$R^2$ is
azido
substituted amino
halogen
acyloxy
alkoxy
aryloxy or
aralkoxy.

The starting methyleneamine compound (I), wherein n is an integer of three, can be also represented by the following formula:

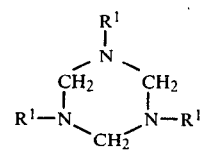

wherein $R^1$ is as defined above.

The reaction of the present invention is conducted by reacting methyleneamine compound (I) with substituted acetic acid (II) or its reactive derivative of the carboxy function in the presence of a Lewis acid and a base.

The starting methyleneamine compounds (I) are new and can be prepared, for instance, by a process as shown in the following scheme.

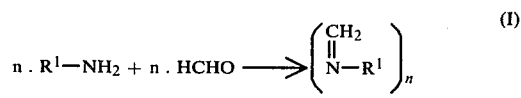

wherein $R^1$ and n are each as defined above.

It is to be understood that the "organic residue bearing a carboxy group or its derivative" of the definition for the symbol $R^1$ of the compounds (I) and (III) includes:
aromatic hydrocarbon radical bearing always a carboxy group or its derivative;
aliphatic hydrocarbon radical bearing always a carboxy group or its derivative; and
aromatic-aliphatic hydrocarbon radical bearing always a carboxy group or its derivative;
in which the aliphatic hydrocarbon moiety of the aliphatic and aromatic-aliphatic hydrocarbon radicals may be substituted with suitable substituent(s), and an optional aliphatic carbon atom of above mentioned aliphatic and aromatic-aliphatic hydrocarbon radicals may be replaced by a hetero-atom, and the aromatic moiety of aromatic and aromatic-aliphatic hydrocarbon radicals may be substituted with suitable substituent(s).

Suitable radicals as stated above will be explained in more concrete and detail in the following.

(1) Regarding the aromatic hydrocarbon radical bearing always a carboxy group or its derivative, the aromatic hydrocarbon residue therein includes aryl group, whose examples are phenyl, tolyl, xylyl, mesityl, naphthyl and the like, and the said aromatic hydrocarbon residue may be substituted by suitable substituent(s) as shown below.

(2) Regarding the aliphatic hydrocarbon radical bearing always a carboxy group or its derivative, in which an optional carbon atom may be replaced by a heteroatom, for example, oxygen, sulfur and the like.

The above-defined aliphatic hydrocarbon residue includes alkyl (e.g. methyl, ethyl, propyl, isopropyl, butyl, isobutyl, sec-butyl, tert-butyl, pentyl, isopentyl, neopentyl, etc.); alkenyl (e.g. vinyl, 1-propenyl, allyl, isopropenyl, butenyl, 1- or 2-methylpropenyl, pentenyl, etc.); alkynyl (e.g. ethynyl, propynyl, butynyl, 1- or 2-methyl propynyl, pentynyl, etc.); alkoxyalkyl (e.g. methoxymethyl, ethoxymethyl, methoxyethyl, etc.); alkoxyalkenyl (e.g. methoxyvinyl, methoxypropenyl, etc.); alkoxyalkynyl (e.g. methoxyethynyl, ethoxypropynyl, etc.); alkylthioalkyl (e.g. methylthiomethyl, ethylthiomethyl, ethylthioethyl, etc.); alkylthioalkenyl (e.g. methylthiovinyl, methylthiopropenyl, ethylthiopropenyl, etc.); and alkylthioalkynyl (e.g. methylthioethynyl, methylthiopropynyl, etc.).

The said aliphatic hydrocarbon residue may be substituted by suitable substituent(s) as shown below, and it is to be understood that suitable aliphatic hydrocarbon residue comprises up to 8 carbon atoms, preferably 1 to 6 and more preferably 1 to 3 carbon atom(s).

In connection with the above definitions, it is to be noted that, among the aliphatic hydrocarbon radical bearing always a carboxy group or its derivatives, preferred embodiment is $C_1$–$C_2$alkyl bearing a carboxy group or its ester, and more preferred one is methyl bearing a carboxy group or its ester, the definitions of which can naturally and clearly be derived from the explanation of the definitions as explained above.

In this respect, the meaning of the ester is referred to the following explanation.

(3) Regarding the aromatic-aliphatic hydrocarbon radical bearing always a carboxy group or its derivative at the aliphatic hydrocarbon moiety therein includes aromatic carbocycle substituted-aliphatic hydrocarbon residue and aromatic heterocycle substituted-aliphatic hydrocarbon residue. An optional aliphatic carbon atom of said aromatic-aliphatic hydrocarbon residue may be replaced by a hetero-atom, for example, oxygen, sulfur and the like, and the aliphatic hydrocarbon moiety is the same as illustrated above (i.e. alkyl, alkenyl and alkynyl). The particulars of said residue may be as follows.

(i) The aromatic carbocycle substituted-aliphatic hydrocarbon residue includes aryl-aliphatic hydrocarbon residue, in which the examples of the aryl and aliphatic hydrocarbon moieties thereof are referred to those of the corresponding residue as illustrated in the above para. (1) and (2), respectively.

Suitable aryl-aliphatic hydrocarbon residue includes: aralkyl (e.g. benzyl, phenethyl, 1-phenylethyl, phenylpropyl, phenylbutyl, phenylpentyl, tolylmethyl, tolylethyl, tolylpropyl, xylylmethyl, xylylethyl, xylypropyl, mesitylmethyl, mesitylethyl, mesitylpropyl, naphthylmethyl, naphthylethyl, naphthylpropyl, naphthylbutyl, diphenylmethyl, diphenylethyl, diphenylpropyl, etc.); aralkenyl (e.g. styryl, cinnamyl, phenylbutenyl, phenylpentenyl, tolylvinyl, tolylpropenyl, tolylbutenyl, xylylvinyl, xylylpropenyl, mesitylvinyl, naphthylvinyl, naphthylpropenyl, etc.); and the like.

In the above aryl-aliphatic hydrocarbon residue, an optional aliphatic carbon atom may be replaced by a hetero-atom, for example, oxygen, sulfur, etc., and the examples thereof are as follows: aryloxyalkyl (e.g. phenoxymethyl, phenoxyethyl, tolyloxymethyl, naphthoxyethyl, etc.); aryl-substituted-alkoxyalkyl (e.g. α-methoxybenzyl, α- or β-methoxyphenethyl, α- or β-ethoxyphenethyl, α- or β-propoxyphenethyl, α-, β- or γ-methoxyphenylpropyl, α-, β- or γ-ethoxyphenylpropyl, etc.); aryloxyalkenyl (e.g. phenoxyvinyl, phenoxypropenyl, naphthoxypropenyl, etc.); aryl-substituted-alkoxyalkenyl (e.g. α- or β-methoxystyryl, α-, β- or γ-methoxycinnamyl, α-, β- or γ-ethoxycinnamyl, etc.); arylthioalkyl (e.g. phenylthiomethyl, phenylthioethyl, phenylthiopropyl, phenylthiobutyl, tolylthiomethyl, tolylthioethyl, xylylthioethyl, xylylthiopropyl, mesitylthiobutyl, naphthylthiomethyl, napthylthioethyl, naphthylthiopropyl, etc.); arylthioalkenyl (e.g. phenylthiovinyl, phenylthiopropenyl, phenylthiobutenyl, tolylthiovinyl, xylylthiopropenyl, naphthylthiovinyl, naphthylthiopropenyl, etc.); aralkyloxyalkyl (e.g. benzyloxymethyl, benzyloxyethyl, phenethyloxyethyl, tolylmethoxyethyl, benzyloxypropyl, etc); aralkylthioalkyl (e.g. benzylthioethyl, phenethylthiopropyl, etc.); aralkyloxyalkenyl (e.g. benzyloxypropenyl, phenethyloxyvinyl, etc.); aralkylthioalkenyl (e.g. benzylthiovinyl, benzylthiopropenyl, etc.); and the like.

(ii) The aromatic heterocycle substituted-aliphatic hydrocarbon residue includes 5 to 10 membered aromatic heterocycle substituted-aliphatic hydrocarbon residue, in which the heterocycle moiety is, more particularly, 5 to 6 membered monocyclic heterocycle or 9 to 10 membered, fushed heterocycle containing at least one hetero-atom selected from nitrogen, oxygen and sulfur. And the aliphatic hydrocarbon moiety is refered to the one as mentioned in the above para. (2). An optional aliphatic carbon atom may be replaced with a hetero-atom, for example, oxygen, sulfur, etc. Suitable examples of the aromatic heterocycle substituted-aliphatic hydrocarbon residue are illustrated as follows: heterocyclic-alkyl such as thienylalkyl (e.g. thienylmethyl, thienylethyl, thienylpropyl, thienylbutyl, dithienylpropyl, etc.), furylalkyl (e.g. furylmethyl, furylethyl, furylpropyl, difurylbutyl, etc.), pyridylalkyl (e.g. pyridylmethyl, pyridylethyl, pyridylpropyl, etc.), pyrrolylalkyl (e.g. pyrrolylmethyl, pyrrolylethyl, etc.), imidazolylalkyl (e.g. imidazolylmethyl, imidazolylethyl, etc.), pyrimidinylalkyl (e.g. pyrimidinylmethyl, pyrimidinylethyl, etc.), thiazolylalkyl (thiazolylmethyl, thiazolylethyl, etc.), oxazolylalkyl (e.g. oxazolylmethyl, oxazolylethyl, etc.), thiadiazolylalkyl (e.g. thiadiazolylmethyl, thiadiazolylethyl, etc.), oxadiazolylalkyl (e.g. oxadiazolylmethyl, oxadiazolylethyl, etc.), isoxazolylalkyl (e.g. isoxazolylmethyl, isoxazolylethyl, etc.), isothiazolylalkyl (e.g. isothiazolylmethyl, isothiazolylethyl, etc.), triazolylalkyl (e.g. triazolylmethyl, triazolylethyl, etc.), tetrazolylalkyl (e.g. tetrazolylmethyl, tetrazolylethyl, etc.), indolylalkyl (e.g. indolylmethyl, indolylethyl, etc.), purinylalkyl (e.g. purinylmethyl, purinylethyl, etc.), benzimidazolylalkyl (e.g. benzimidazolylmethyl, benzimidazolylethyl, etc.), benzotriazolylalkyl (e.g. benzotriazolylmethyl, benzotriazolylethyl, etc.), quinolylalkyl (e.g. quinolylmethyl, quinolylethyl, etc.), benzofurylalkyl (e.g. benzofurylmethyl, benzofurylethyl, etc.), benzothienylalkyl (e.g. benzothienylmethyl, benzothienylethyl, etc.), benzoxazolyalkyl (e.g. benzoxazolylmethyl, benzoxazolylethyl, etc.); heterocyclic-alkenyl such as thienylalkenyl (e.g. thienylvinyl, thienylpropenyl, thienylbutenyl, etc.), furylalkenyl (e.g. furylvinyl, furylpropenyl, etc.), pyridylalkenyl (e.g. pyridylvinyl, pyridylpropenyl, etc.), isoxazolylalkenyl (e.g. isoxazolylvinyl, isoxazolylpropenyl, etc.), isothiazolyl alkenyl (e.g. isothiazolylvinyl, isothiazolylpropenyl, etc.), oxazolylalkenyl (e.g. oxazolylvinyl, oxazolylpropenyl, etc.), oxadiazolylalkenyl (e.g. oxadiazolylvinyl, oxadiazolylpropenyl, etc.), thiazolylalkenyl (e.g. thiazolylvinyl, thiazolylbutenyl, etc.), thiadiazolylalkenyl (e.g. thiadiazolylpropenyl, thiadiazolylbutenyl, etc.); heterocyclicoxyalkyl (e.g. thienyloxyethyl, furyloxymethyl, pyridyloxyethyl, etc.); heterocyclicthioalkyl (e.g. thienylthiomethyl, furylthioethyl, pyridylthioethyl, thiazolylthiomethyl, thiadiazolylthiomethyl, triazolylthiomethyl, tetrazolylthiomethyl, benzothiazolylthiomethyl, oxazolythioethyl, thiadiazolylthiopropyl, etc.); heterocycle-substituted-alkoxyalkyl (thenyloxy methyl, furfuryloxy methyl, etc.); heterocyclicthioalkenyl (thienylthiovinyl, furythioallyl, etc.); and the like.

In the above aromatic (including aromatic carbocyclic and aromatic heterocyclic)-aliphatic hydrocarbon residue, each of the aromatic moiety and aliphatic hydrocarbon moiety may be substituted by suitable substituent(s) as illustrated below, and it is to be understood that the suitable aliphatic hydrocarbon moiety thereof is the same as illustrated above and comprises up to 8 carbon atoms, preferably 1 to 6 and more preferably 1 to 4 carbon atom(s).

In connection with the above definitions, it is to be noted that, among the aromatic-aliphatic hydrocarbon radical bearing always a carboxy group or its derivative at the aliphatic hydrocarbon moiety, preferred embodiment is phenylthio-$(C_1-C_2)$alkyl bearing a carboxy group or its ester at the alkyl moiety; phenyl-substituted-$(C_1-C_2)$alkoxy-$(C_1-C_2)$alkyl bearing a carboxy group or its ester at the alkyl moiety; $C_6-C_{10}$aryl-$(C_1-C_2)$alkyl bearing a carboxy group or its ester at the alkyl moiety, in which the aryl moiety may be substituted with a protected hydroxy group; and 5-membered aromatic monocyclic heterocyclic-$(C_1-C_2)$alkyl bearing a carboxy group or its ester at the alkyl moiety, in which said heterocyclic moiety contains one heteroatom selected from oxygen and sulfur atoms. Further, the more preferred embodiment is phenylthioethyl bearing a carboxy group or its ester at the first position of the ethyl moiety; β-methoxyphenethyl bearing a carboxy group or its ester at the α-position of the phenethyl moiety; benzyl bearing a carboxy group or its ester at the α-position, in which the phenyl moiety may be substituted with a protected hydroxy group; phenethyl bearing a carboxy group or its ester at the α- or β-position, in which the phenyl moiety may be substituted with a protected hydroxy group; naphthylmethyl bearing a carboxy group or its ester at the methyl moiety; thienylmethyl bearing a carboxy group or its ester at the methyl moiety; and furylmethyl bearing a carboxy group or its ester at the methyl moiety, respectively, all of the definitions for $R^1$ of the abovementioned and preferred compounds of this invention can naturally and clearly be derived from the explanation of the definitions as explained above and below, and lots of the working examples below.

In this respect, the meanings of the protected hydroxy group and the ester can be definitely referred to the following explanation.

As the suitable substituent as stated in the explanation of the radicals in the above para. (1), (2) and (3), there may be illustrated a substituent such as amino, azido, cyano, halogen (e.g. chlorine, bromine, etc.), hydroxy, mercapto, nitro, sulfo, alkoxy (e.g. methoxy, ethoxy, propoxy, isopropoxy, butoxy, isobutoxy, sec-butoxy, etc.), alkanesulfonylamino (e.g. mesylamino, ethanesulfonylamino, propanesulfonylamino, 1-methylethanesulfonylamino, butanesulfonylamino, 1- or 2-methylpropane-sulfonylamino, etc.), and the like.

It is to be understood that such substituents do not adversely participate in the reaction of the present invention.

With regard to the substituents as illustrated above, more preferable substituent for each of the moieties is mentioned as follows, that is a substituent for the aliphatic hydrocarbon moiety in the residue as stated and illustrated in the above para. (2) and (3) may be halogen, hydroxy, amino, alkanesulfonamido, mercapto etc.;

a substituent for the aromatic hydrocarbon moiety in the residue as stated and illustrated in the above para. (1) and (3) may be halogen, alkoxy, hydroxy, amino, alkanesulfonamido mercapto, azido, cyano, nitro, sulfo, etc.; and a substituent for the aromatic heterocycle moiety in the residue as stated and illustrated in the above para. 3) may be alkyl (e.g. methyl, ethyl, propyl, butyl, etc.), halogen, amino, hydroxy, alkanesulfonamido, nitro, etc.

In the above substituents, hydroxy, amino, alkanesulfonamido and mercapto groups may be optionally protected by a suitable protective group, respectively.

Suitable protective group of amino and alkanesulfonamido groups includes conventional protective group, i.e. acyl such as substituted or unsubstituted alkoxycarbonyl (e.g. methoxycarbonyl, ethoxycarbonyl, propoxycarbonyl, butoxycarbonyl, tert-butoxycarbonyl, chloromethoxycarbonyl, bromoethoxycarbonyl, tribromoethoxycarbonyl, trichloroethoxycarbonyl, etc.), substituted or unsubstituted aralkoxycarbonyl (e.g. benzyloxycarbonyl, phenethyloxycarbonyl, diphenylmethoxycarbonyl, nitrobenzyloxycarbonyl, bromobenzyloxycarbonyl, methoxybenzyloxycarbonyl, etc.), substituted or unsubstituted alkanoyl (e.g. formyl, acetyl, propionyl, butyryl, valeryl, dichloroacetyl, trifluoroacetyl, N-phthaloylglycyl, etc.), and the like; substituted or unsubstituted aralkyl (e.g. benzyl, diphenylmethyl, trityl, bromobenzyl, nitrobenzyl, methoxybenzyl, etc.); substituted or unsubstituted aralkylidene (e.g. benzylidene, salicylidene, etc.); substituted or unsubstituted alkylidene, or the corresponding alkenyl such as isopropylidene, 1-alkyl-2-alkoxycarbonylvinyl or 1-alkoxycarbonylmethylalkylidene (e.g. 1-methyl-2-ethoxycarbonylvinyl or 1-ethoxycarbonylmethylethylidene, etc.), or 1-alkyl-2-alkanoylvinyl or 1-(2-oxoalkyl)alkylidene (e.g. 1-methyl-2-acetylvinyl or 1-acetonylethylidene, etc.); and the like.

Suitable protective group of hydroxy and mercapto groups includes substantially the same acyl and aralkyl as illustrated above for the protective group of the amino and alkanesulfonamido, and additionally acyl such as substituted or unsubstituted aroyl (e.g. benzoyl, toluoyl, 4-bromobenzoyl, salicyloyl, etc.), and the like.

With respect to the term "its derivative" in the "organic residue bearing a carboxy group or its derivative" for $R^1$, the "derivative" is intended to mean the one of the carboxy function and includes acid amide, ester, nitrile and the like as illustrated in the following.

Suitable acid amides include:
acid amide, N-alkyl acid amide (e.g. N-methyl acid amide, N-ethyl acid amide, etc.), N,N-dialkyl acid amide (e.g. N,N-diemthyl acid amide, N,N-diethyl acid amide, N-ethyl-N-methyl acid amide, etc.), N-phenyl acid amide, acid amide with pyrazole, imidazole or 4-alkylimidazole (e.g. 4-methylimidazole, 4-ethylimidazole, etc), and the like.

Suitable esters include:
silyl ester, aliphatic ester, containing an aromatic or a heterocyclic group and ester with a N-hydroxy compound.

Suitable silyl ester includes trialkylsilyl (e.g. trimethylsilyl, triethylsilyl, etc.) ester, and the like.

Suitable aliphatic ester includes saturated or unsaturated, acyclic or cyclic aliphatic ester, in which acyclic aliphatic ester may be branched, such as alkyl (e.g. methyl, ethyl, propyl, isopropyl, butyl, tert-butyl, octyl, nonyl, undecyl, etc.) ester; alkenyl (e.g. vinyl, 1-propenyl, allyl, 3-butenyl, etc.) ester; alkynyl (e.g. 3-butynyl, 4-pentynyl, etc.) ester; cycloalkyl (e.g. cyclopentyl, cyclohexyl, cycloheptyl, etc.) ester; and the like. In the above aliphatic ester, the aliphatic moiety may optionally have suitable substituent(s) such as cycloalkyl (e.g. cyclopropyl, cyclohexyl, etc.), alkoxy (e.g. methoxy, ethoxy, propoxy, isopropoxy, butoxy, tert-butoxy, etc.), alkanoyloxy (e.g. acetoxy, propionyloxy, pivaloyloxy, etc.), alkylthio (e.g. methylthio, ethylthio, propylthio, etc.), alkanesulfinyl (e.g. methanesulfinyl, ethanesulfinyl, propanesulfinyl, etc.), alkanesulfonyl (e.g. mesyl, ethanesulfonyl, etc.), phenylazo, halogen (e.g. chlorine, bromine, fluorine, etc.), cyano, nitro, dialkylamino (e.g. dimethylamino, diethylamino, etc.) etc. Prefered examples of such an ester are illustrated more concretely as mono(di or tri)haloalkyl (e.g. chloromethyl, bromoethyl, dichloromethyl, 2,2,2-trichloroethyl, 2,2,2-tribromoethyl, 2,2,2-trifluoroethyl, etc.) ester, cyanoalkyl (e.g. cyanomethyl, cyanoethyl, etc.) ester, cycloalkyl-substituted-alkyl (e.g. 1-cyclopropylethyl, etc.) ester, dialkylaminoalkyl (e.g. dimethylaminoethyl, dimethylaminopropyl, etc.) ester, and the like.

Suitable ester containing an aromatic ring includes for example, aryl (e.g. phenyl, tolyl, xylyl, naphthyl, indanyl, dihydroanthryl, etc.) ester; aralkyl (e.g. benzyl, phenethyl, etc.) ester; aralkenyl (e.g. cinnamyl, etc.) ester; aryloxyalkyl (e.g. phenoxymethyl, phenoxyethyl, phenoxypropyl, etc.) ester; arylthioalkyl (e.g. phenylthiomethyl, phenylthioethyl, phenylthiopropyl, etc.) ester; arenesulfinylalkyl (e.g. benzenesulfinylmethyl, benzenesulfinylethyl, etc.) ester; aroylalkyl (e.g. benzoylmethyl, toluoylethyl, etc.) ester; and the like. Said aromatic ring may opptionally have suitable substituent(s) such as those given in the above aliphatic ester, and additionally, alkyl, hydroxy or the like. Preferably examples of such a substituted ester include halophenyl (e.g. 4-chlorophenyl, 3,5-dibromophenyl, pentachlorophenyl, etc.) ester; halophenylaklyl (e.g. 3,4-dichlorobenzyl, etc.) ester; alkoxyphenyl (e.g. 4-methoxyphenyl, etc.) ester; alkoxyphenylalkyl (e.g. 4-methoxybenzyl, 3,4,5-trimethoxybenzyl, 3,4,5-trimethoxyphenylpropyl, etc.) ester; 4-hydroxy-3,5-di-tert-butylbenzyl ester; and the like.

Suitable ester containing a heterocyclic ring includes heterocyclic ester, heterocyclic-alkyl ester, and the like.

Suitable heterocyclic ester includes saturated or unsaturated, monocyclic or fused, 3 to 10-membered heterocyclic group containing 1 to 4 hetero-atom(s) such as an oxygen, sulfur and nitrogen atom, and said heterocycle may have suitable substituent(s) selected from the same as illustrated as a substituent for aliphatic moiety and aromatic ring of the aforementioned esters. Preferable heterocyclic ester as defined above may be pyridyl ester, picolyl ester, tetrahydropyranyl ester, tetrahydrofuryl ester, quinolyl ester, pyrazolyl ester, and the like, and preferable heterocyclic-alkyl ester includes, for example, aforementioned heterocyclic group-substituted-alkyl (e.g. methyl, ethyl, propyl, etc.) ester such as pyridylmethyl ester, furfuryl ester, 1,4-dioxanylmethyl ester, pyrrolidinylethyl ester, 4-methylpiperazinylethyl ester, and the like.

Suitable ester with a N-hydroxy compound includes the ester with N,N-dialkylhydroxylamine (e.g. N,N-dimethylhydroxylamine, N,N-diethylhydroxylamine, N,N-dipropylhydroxylamine, etc.), the ester with an aldoxime or a ketoxime (e.g. propanal oxime, butanal oxime, acetoxime, benzophenoneoxime, p-bromoacetophenoneoxime, etc.), the ester with N-hydroxyimide (e.g. N-hydroxyphthalimide, N-hydroxysuccimide, etc.), the ester with N-hydroxybenzotriazole (e.g. 6-chloro-1-hydroxybenzotriazole, etc.) and the like.

The definitions for $R^2$ of the compound (II) and (III) are illustrated hereinbelow.

(a) Substituted amino includes protected amino such as acylamino, aralkyl amino, and the like, and is illustrated in more detail in the following;

(i) Acylamino includes, for example, an aliphatic acylamino, an aromatic acylamino, an araliphatic acylamino, a heterocyclic acylamino and a heterocyclic-aliphatic acylamino, and acylamino represented by the formula:

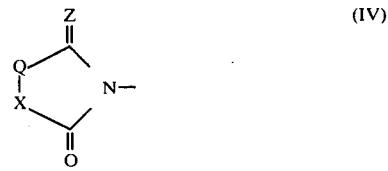

wherein Q is oxy or aryl methylene, X is carbonyl or imino, and Z is oxo, or aryl- or heterocycle-substituted methylene, or

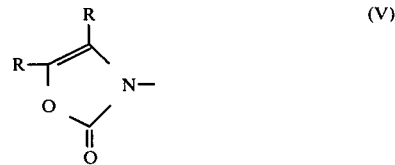

wherein R is aryl.

Suitable acyl moiety in the above acylamino groups including aliphatic acyl, aromatic acyl, araliphatic acyl, heterocyclic acyl and heterocyclic-aliphatic acyl moieties may be illustrated as follows.

Aliphatic acyl such as: alkanoyl (e.g. formyl, acetyl, propionyl, butyryl, isobutyryl, valeryl, isovaleryl, pivaloyl, lauroyl, palmitoyl, succinyl, etc.); alkenoyl (e.g. acryloyl, methacryloyl, crotonoyl, isocrotonoyl, maleoyl, etc.); alkanesulfonyl (e.g. mesyl, ethanesulfonyl, propanesulfonyl, butanesulfonyl, etc.); alkenesulfonyl (e.g. ethylenesulfonyl, propenesulfonyl, etc.); alkoxycarbonyl (e.g. methoxycarbonyl, ethoxycarbonyl, propoxycarbonyl, isopropoxycarbonyl, butoxycarbonyl, tert-butoxycarbonyl, pentyloxycarbonyl, etc.); dialkylphosphoryl (e.g. dimethylphosphoryl, diethylphosphoryl, diisopropylphosphoryl, etc.); and the like.

Aromatic acyl such as: aroyl (e.g. benzoyl, toluoyl, xyloyl, naphthoyl, phthaloyl, etc.); arenesulfonyl (e.g. benzenesulfonyl, toluenesulfonyl, xylenesulfonyl, naphthalenesulfonyl, etc.); diarylphosphoryl (e.g. diphenylphosphoryl. etc.); and the like.

Araliphatic acyl such as: aralkanoyl (e.g. phenylacetyl, tolylacetyl, xylylacetyl, naphthylacetyl, biphenylylacetyl, phenylpropionyl, tolylpropionyl, naphthylpropionyl, 2-methyl-3-phenylpropionyl, 2-methyl-2-phenylpropionyl, 2-methyl-3-naphthylpropionyl, phenylbutyryl, naphthylbutyryl, phenylvaleryl, tolylvaleryl, naphthylvaleryl, diphenylacetyl, diphenylpropionyl, etc.); aralkanesulfonyl (e.g. phenylmesyl, tolylmesyl, naphthylmesyl, phenylethanesulfonyl, naphthylethanesulfonyl, phenylpropanesulfonyl, phenylbutanesulfonyl, etc.); aralkenesulfonyl (e.g. phenylethylenesulfonyl, tolylethylenesulfonyl, naphthylethylenesulfonyl, phenylpropenesulfonyl, naphthylpropenesulfonyl, phenylbutenesulfonyl, etc.); aralkoxycarbonyl (e.g. benzyloxycarbonyl, phenethyloxycarbonyl, phenylpropoxycarbonyl, benzhydryloxycarbonyl, etc.); diaralkylphosphoryl (e.g. dibenzylphosphoryl, etc.); and the like.

Heterocyclic acid such as: heterocycle-carbonyl containing 3 to 10 membered monocyclic or fused heterocyclic group having 1 to 4 hetero-atom(s) selected from nitrogen, oxygen and sulfur (e.g. aziridinecarbonyl, azetidinecarbonyl, pyrrolecarbonyl, 2H-pyrrolecarbonyl, imidazolecarbonyl, pyrazolecarbonyl, nicotinoyl, isonicotinoyl, pyrazinecarbonyl, piperidinecarbonyl, piperazinecarbonyl, pyrimidinecarbonyl, pyridazinecarbonyl, triazolecarbonyl, thiazolinecarbonyl, triazinecarbonyl, pyrrolidinecarbonyl, imidazolidinecarbonyl, oxiranecarbonyl, furoyl, pyrancarbonyl, thenoyl, morpholinecarbonyl, furazanecarbonyl, oxazolecarbonyl, isoxazolecarbonyl, thiazolecarbonyl, thiadiazolecarbonyl, oxadiazolecarbonyl, indolecarbonyl, 3H-indolecarbonyl, isoindolecarbonyl, indolizinecarbonyl, 1H-indazolecarbonyl, purinecarbonyl, benzimidazolecarbonyl, benzotriazolecarbonyl, quinolinecarbonyl, isoquinolinecarbonyl, naphthyridinecarbonyl, quinoxalinecarbonyl, quinazolinecarbonyl, benzofurancarbonyl, chromenecarbonyl, isobenzofurancarbonyl, benzothiophenecarbonyl, xanthenecarbonyl, benzoxazolecarbonyl, benzisoxazolecarbonyl, benzothiazolecarbonyl, etc.);

Heterocyclic-aliphatic acyl such as: heterocyclic-alkanoyl [e.g. thienylacetyl, furylacetyl, pryridylacetyl, (pyridyl-1-oxide)acetyl, pyrrolylacetyl, imidazolylacetyl, pyrazolylacetyl, triazolylacetyl, tetrazolylacetyl, oxazolylacetyl, oxadiazolylacetyl, thiazolylacetyl, thiazolinylacetyl, thiadiazolylacetyl, morpholinylacetyl, pyranylacetyl, pyrrolidinylacetyl, pyrrolinylacetyl, benzothienylacetyl, benzoxadiazolylacetyl, benzothiazolylacetyl, benzoxazolylacetyl, benzisoxazolylacetyl, benzotriazolylacetyl, indolylacetyl, purinylacetyl, thienylpropionyl, furylpropionyl, pyridylpropionyl, imidazolylpropionyl, oxazolylpropionyl, oxadiazolylpropionyl, thiazolylpropionyl, thiadiazolylpropionyl, purinylpropionyl, indolylpropionyl, etc.];

In acylamino represented by the formulae (IV) and (V), suitable aryl for the symbol R and aryl moiety in the definition of the symbols Q and Z includes phenyl, tolyl, xylyl, mesityl, naphthyl and the like, and suitable heterocyclic group in the definition of the symbol Z includes the same as heterocyclic moiety illustrated for the heterocyclic-carbonyl in the acylamino as mentioned above.

(ii) Suitable aralkylamino includes benzylamino, phenethylamino, phenylpropylamino, diphenylmethylamino, tritylamino, tolylmethylamino, tolylethylamino, xylylmethylamino, naphthylmethylamino and the like.

(b) Suitable halogen includes chlorine, bromine, iodine and the like.

(c) Suitable acyl moiety in the acyloxy may be substantially the same as those illustrated for the acyl moiety of the aforementioned acylamino other than those of the formulae (IV) and (V).

(d) Suitable alkoxy includes methoxy, ethoxy, propoxy, isopropoxy, butoxy, isobutoxy, tert-butoxy and the like.

(e) Suitable aryloxy includes phenoxy, tolyloxy, xylyloxy, naphthoxy and the like.

(f) Suitable aralkoxy includes benzyloxy, phenethyloxy, phenylpropoxy, phenylbutoxy, diphenylmethoxy, trityloxy, naphthylmethoxy, tolylmethoxy, tolylethoxy, xylylethoxy, and the like.

Further, the aliphatic hydrocarbon moiety, aromatic hydrocarbon moiety and heterocyclic moiety in the substituted amino, acyloxy, alkoxy, aryloxy, aralkoxy as exemplified above for $R^2$ may have one or more suitable substituent(s) selected from those given in the description of suitable examples of the substituents in the organic residue bearing a carboxy or its derivative for $R^1$ of the compound (I) and (III). And additionally, the aliphatic hydrocarbon moiety in the above substituted amino group may have oxo, hydroxyimino or substituted imino such as alkoxyimino (e.g. methoxyimino, ethoxyimino, propoxyimino, etc.), aryloxyimino (e.g. phenoxyimino, etc.), aralkoxyimino (e.g. benzyloxyimino, phenethyloxyimino, etc.), alkoxycarbonylalkoxyimino (e.g. ethoxycarbonylmethoxyimino, etc.) and the like.

In these substituents as mentioned above, amino, alkanesulfonamido hydroxy and carboxy may be protected preferably by suitable protective groups selected from those as illustrated in the aforementioned substituents of the organic residue for $R^1$, respectively, and hydroxyimino may also be protected by the same protective group as illustrated for the hydroxy.

As to the object compound of the present invention, the preferred embodiment is the compound of the following formula, the definitions of which are selected automatically from and on the basis of the aforementioned disclosure concerning the definitions for $R^1$ and $R^2$:

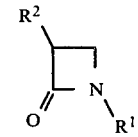

wherein $R^1$ is $C_1$–$C_2$alkyl bearing a carboxy group or its ester; phenylthio-$(C_1$–$C_2)$alkyl bearing a carboxy group or its ester at the alkyl moiety; phenylsubstituted-$(C_1$–$C_2)$alkoxy-$(C_1$–$C_2)$alkyl bearing a carboxy group or its ester at the alkyl moiety; $C_6$–$C_{10}$aryl-$(C_1$–$C_2)$alkyl bearing a carboxy group or its ester at the alkyl moiety, in which the aryl moiety may be substituted with a protected hydroxy group; and 5-membered aromatic monocyclic heterocyclic$(C_1$–$C_2)$alkyl bearing a carboxy group or its ester at the alkyl moiety, in which said heterocyclic moiety contains one hetero-atom selected from oxygen and sulfur atoms; and $R^2$ is azido or protected amino.

Further, it is to be noted that the more preferred embodiment of the object compound of the present invention is the compound of the following formula, the definition of which also are automatically and more specifically selected from and on the basis of the aforementioned disclosure concerning the definitions for $R^1$ and $R^2$:

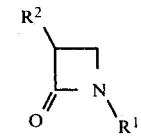

wherein $R^1$ is methyl bearing a carboxy group or its ester; phenylthioethyl bearing a carboxy group or its ester at the first position of the ethyl moiety; β-methoxyphenethyl bearing a carboxy group or its ester at the α-position of the phenethyl moiety; benzyl bearing a carboxy group or its ester at the α-position, in which the phenyl moiety may be substituted with a protected hydroxy group; phenethyl bearing a carboxy group or its ester at the α-or β-position, in which the phenyl moiety may be substituted with a protected hydroxy group; naphthylmethyl bearing a carboxy group or its ester at the methyl moiety; thienylmethyl bearing a carboxy group or its ester at the methyl moiety; and furylmethyl bearing a carboxy group or its ester at the methyl moiety, and $R^2$ is azido or protected amino. In the above definitions, numbering system relating to the first position, α-position and β-position is used according to that of International Union of Pure and Applied Chemistry.

For reference, the numbering of the above definitions is illustrated with the formula:

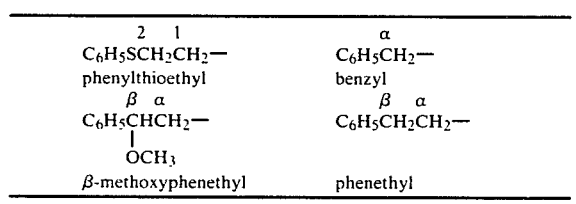

With respect to the reactive derivatives at the carboxy of the compound (II):

The "reactive derivative" at the carboxy includes an acid anhydride, ester, acid halide, acid amide, acid azide, a salt with a base and the like.

Suitable acid anhydride includes mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, hydrohalogenic acid (e.g. hydrochloric acid, hydrobromic acid, etc.), sulfuric acid, monoalkyl carbonate (e.g. methyl carbonate, ethyl carbonate, propyl carbonate, etc.), aliphatic carboxylic acid (e.g. acetic acid, pivalic acid, pentanoic acid, isopentanoic acid, 2-ethylbutyric acid, trichloroacetic acid, trifluoroacetic acid, etc.), aromatic carboxylic acid (e.g. benzoic acid, etc.), or symmetrical acid anhydride and the like.

Suitable ester includes preferably conventional activated ester, such as substituted alkyl ester (e.g. cyanomethyl ester, methoxymethyl ester, etc.), alkenyl ester (e.g. vinyl ester, etc.), alkynyl ester (e.g. propargyl ester, etc.), substituted aryl ester (e.g. 4-nitrophenyl ester, 2,4-dinitrophenyl ester, trichlorophenyl ester, etc.), heterocyclic ester (e.g. tetrahydropyranyl ester) and other ones as illustrated for the "derivative" of carboxy, such as an ester with N-hydroxycompound (e.g. N,N-dialkylhydroxylamine, ketoxime, N-hydroxyimine, N-hydroxybenzotriazole, etc.) and the like.

Suitable acid amide includes preferably conventional activated amides such as acid amide with pyrazole, imidazole or 4-substituted imidazole (e.g. 4-methylimidazole, etc.) and the like.

Suitable acid halide includes acid chloride, acid bromide, acid iodide and the like.

Suitable salt includes a salt with an organic base such as those given below and a salt with an inorganic base, such as alkalimetal salt (e.g. sodium salt, potassium salt, etc.), alkaline earth metal salt (e.g. calcium salt, magnesium salt, etc.), and the like.

Suitable Lewis acid to be used in the reaction includes halogenated metal or non-metal compound, for example, boron trihalide (e.g. boron trifluoride, boron trichloride, boron tribromide, etc.); a complex of the boron trihalide with a solvent such as ethereal compound (e.g. diethyl ether, tetrahydrofuran, etc.), alcohol (e.g. methanol, etc.), carboxylic acid (e.g. acetic acid, etc.) or the like; alminium halide (e.g., alminium chloride, alminium bromide, etc.); zinc halide (e.g. zinc chloride, etc.); stannic halide (e.g. stannic chloride, etc.); ferric halide (e.g. ferric chloride, etc.); titanium halide (e.g. titanium chloride, etc.); silicon tetrahalide (e.g. silicon tetrachloride, etc.); antimony halide (e.g. antimony chloride, etc.) and the like.

In the above mentioned Lewis acid, boron trifluoride diethyl etherate is the common one and preferably employed in the present invention.

Suitable base to be used in the reaction includes an organic base such as: trialkylamine (e.g. trimethylamine, triethylamine, tributylamine, etc.); N,N-dialkylaniline (e.g. N,N-dimethylaniline, N,N-diethylaniline, etc.); N,N-dialkylaralkylamine (e.g. N,N-dimethylbenzylamine, etc.); N-substituted or unsubstituted heterocyclic compound (e.g. N-methylmorpholine, N-methylpiperidine, pyridine, dimethylaminopyridine, picoline, lutidine, quinoline, 1,5-diazabicyclo-[4,3,0]-5-nonene, 1,4-diazabicyclo[2,2,2,]octane, 1,5-diazabicyclo[5,4,0]-5-undecene, etc.) and the like.

The present reaction can be usually carried out in a conventional solvent such as dichloromethane, chloroform, carbon tetrachloride, diethyl ether, tetrahydrofuran dioxane, pyridine, N,N-dimethylformamide or an optional mixture thereof, or in any other solvent which does not have an adverse influence on the reaction.

The reaction temperature is not restricted, and the reaction is preferably carried out from under cooling to at ambient temperature.

As previously mentioned, the synthesis method of the present invention is characterized by using boron trihalide as a reagent in the reaction. For the purpose of showing the characteristic of use of the boron trihalide for preparing 1,3-disubstituted-2-azetidinone and that the process of this invention is new and special, there are illustrated experiments, in which the compound of the formula is used as one of the starting trimers of C-unsubstituted methyleneamine compound (I):

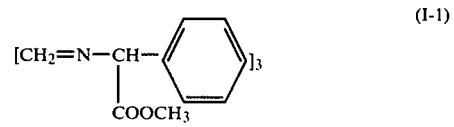
(I-1)

Experiment 1:

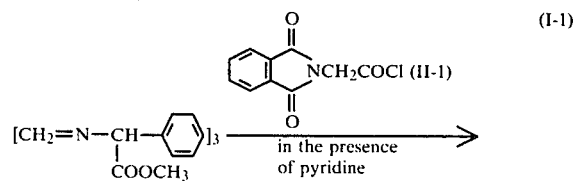
(I-1)

Experiment 1:

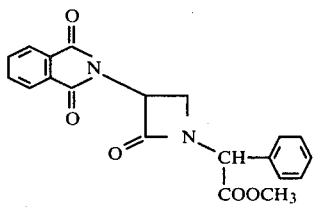

(III-3)

This reaction was carried out by reacting the compound (I-1) with phthalimidoacetyl chloride (II-1) in the presence of pyridine, but the desired compound (III-3) could not be detected.

Experiment 2:

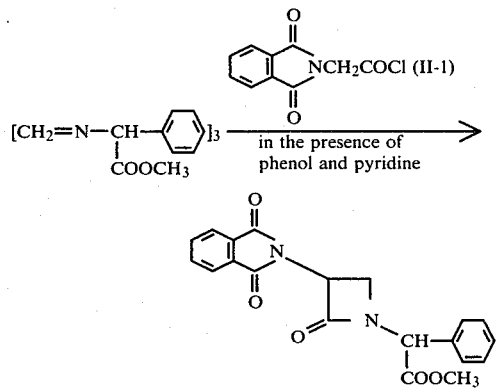

This reaction was carried out by reacting the compound (I-1) with phthalimidoacetyl chloride (II-1) in the presence of pyridine, and of phenol instead of boron trihalide, but the desired compound (III-3) could not be detected.

Experiment 3:

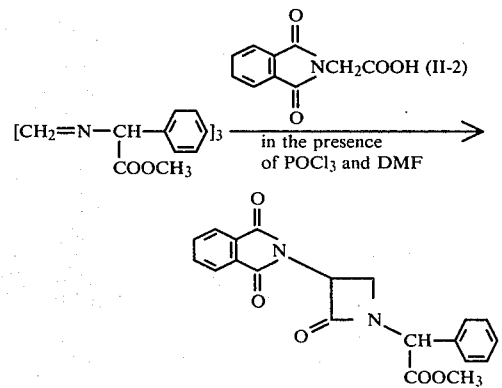

The reaction was carried out by reacting the compound (I-1) with phthalimidoacetic acid (II-2) in the presence of N,N-dimethylformamide and of phosphorus oxychloride instead of boron trihalide but the desired compound (III-3) could not be detected.

Experiment 4:

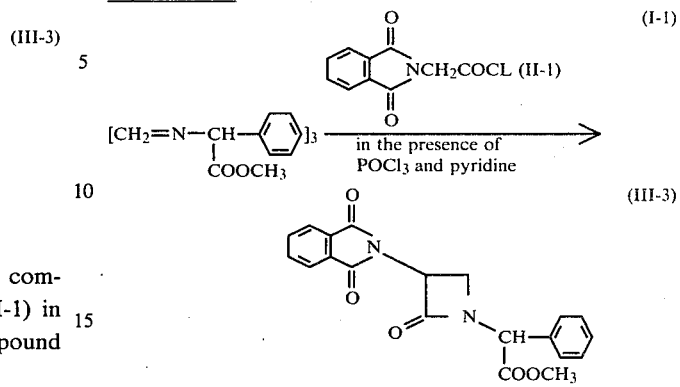

The reaction was carried ut by reacting the compound (I-1) with phthalimidoacetyl chloride (II-1) in the presence of pyridine and of phosphorus oxychloride instead of boron trihalide, but the desired compound could not be detected.

From the results of the above reactions, it can be said that the behavior of boron trihalide to be used in the present invention is clearly different from those of the phenol and phosphorus oxychloride in the above cited prior arts and the use of boron trihalide is an essential factor for preparing 1,3-disubstituted-2-azetidinone (III) of the present invention.

The object compound (III), prepared by the process of the present invention, may be given as a mixture of two epimeric stereoisomers due to the asymmetric carbon atom of the third position of the azetidinone ring, and these mixtures may optionally be resolved, if necessary, into the corresponding stereoisomer according to conventional resolution methods. The object compound (III) of this invention includes a useful antibiotic for the treatment of microbial infections in animals and human being and a useful intermediate for preparing the useful antibiotics. That is, some of the 3-acylamino-2-azetidinone compounds (III) have antimicrobial activities against various pathogenic microorganisms, e.g. *Escherichia coli, Pseudomonas aeruginosa, Staphlococcus aureus*, etc. And further, the object compound (III) having a protected amino or azido at the 3rd position thereof, for example, 3-phthalimido, 3-azido-, 3-(4,5-diphenyl-2-oxo-4-oxazolin-3-yl)-2-azetidinone compounds are important intermediates for preparing the 3-acylamino-2-azetidinone compounds having antimicrobial activity. That is, the object compound (III) can once be converted into 3-amino-2-azetidinone compound by a conventional method and then said 3-amino-2-azetidinone compound is acylated to provide 3-acylamino-2-azetidinone compounds which have antimicrobial activities against various pathogenic microorganisms. In the course of this reaction, in case that the object compound (III) of this invention bears a protected hydroxy and/or a protected carboxy groups at the first position of the azetidine ring, they are subjected to removal reaction optionally before or after each of "conversion reaction to 3-amino-2-azetidinone compound" and "acylation reaction thereof" to the corresponding hydroxy and/or carboxy, by a conventional method. For reference, embodiments of the processes, according to which the object compound of this invention is led to the 3-acylamino-2-azetidinone compound having antimicrobial activity, is shown in reference to use of one of the object compound (III) of this invention as a starting compound, in the following.

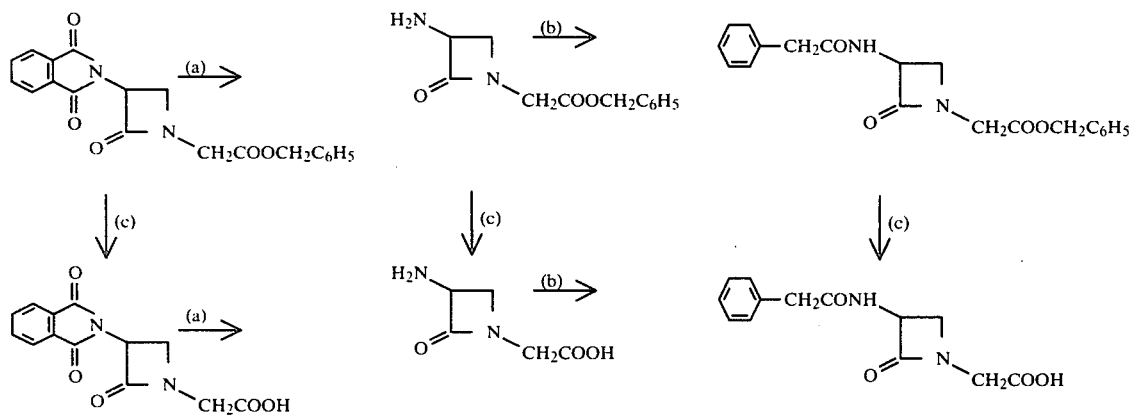

Note:
Reaction (a): Conversion to 3-amino-2-azetidinone compound
Reaction (b): Acylation of 3-amino-2-azetidinone compound to 3-acylamino-2-azetidinone compound
Reaction (c): Removal reaction of protective group Particularly, some examples relating to the conversion of the representative compounds of this invention to the corresponding 3-acylamino-2-azetidinone compound having antimicrobial activity are illustrated in the following.

benzyl 2-(3-phthalimido-2-oxo-1-azetidinyl)acetate to 2-(3-phenylacetamido-2-oxo-1-azetidinyl)acetic acid (Compound A)

methyl 2-(3-phthalimido-2-oxo-1-azetidinyl)-2-phenylacetate to 2-[3-[2-{4-(3-amino-3-carboxypropoxy)phenyl}-2-hydroxyiminoacetamido]-2-oxo-1-azetidinyl]-2-phenylacetic acid (Compound B)

methyl 2-(3-benzyloxycarbonylamino-2-oxo-1-azetidinyl)-2-phenylacetate to the Compound B methyl 2-(3-azido-2-oxo-1-azetidinyl)-2-phenylacetate to the Compound B benzyl 2-(3-phthalimido-2-oxo-1-azetidinyl)-2-phenylacetate to the Compound B methyl 2-[3-(4,5-diphenyl-2-oxo-4-oxazolin-3-yl)-2-oxo-1-azetidinyl]-2-phenylacetate to the Compound B methyl 2-(3-diethylphosphorylamino-2-oxo-1-azetidinyl)-2-phenylacetate to the Compound B methyl 2-(3-phthalimido-2-oxo-1-azetidinyl)-2-(4-benzyloxyphenyl)acetate to 2-[3-[2-{4-(3-amino-3-carboxypropoxy)phenyl}-2-hydroxyiminoacetamido]-2-oxo-1-azetidinyl]-2-(4-hydroxyphenyl)acetic acid (Compound C)

methyl 2-(3-phthalimido-2-oxo-1-azetidinyl)-2-(4-benzyloxycarbonyloxyphenyl)acetate to the Compound C phenacyl 2-(3-phthalimido-2-oxo-1-azetidinyl)-2-(4-phenacyloxyphenyl)acetate to the Compound C benzyl 2-(3-azido-2-oxo-1-azetidinyl)-2-(4-benzyloxyphenyl)acetate to Compound C benzyl 2-(3-phthalimido-2-oxo-1-azetidinyl)-2-(4-benzyloxyphenyl)acetate to the Compound C benzyl 2-(3-phthalimido-2-oxo-1-azetidinyl)-2-(4-benzyloxycarbonyloxyphenyl)acetate to the Compound C methyl 2-(3-phthalimido-2-oxo-1-azetidinyl)-3-phenylthiopropionate to 2-[3-(2-phenyl-2-hydroxyiminoacetamido)-2-oxo-1-azetidinyl]-3-phenylthiopropionic acid (Compound D)

methyl 2-(3-phthalimido-2-oxo-1-azetidinyl)-2-(1-naphthyl)acetate to 2-[3-(2-phenyl-2-hydroxyiminoacetamido)-2-oxo-1-azetidinyl]-2-(1-naphthyl)acetic acid (Compound E)

methyl 2-(3-phthalimido-2-oxo-1-azetidinyl)-3-(4-benzyloxyphenyl)propionate to 2-[3-(2-phenyl-2-hydroxyiminoacetamido)-2-oxo-1-azetidinyl]-3-(4-hydroxyphenyl)propionic acid (Compound F)

methyl 2-(3-phthalimido-2-oxo-1-azetidinyl)-2-(2-thienyl)acetate to 2-[3-[2-{4-(3-amino-3-carboxypropoxy)phenyl}-2-hydroxyiminoacetamido]-2-oxo-1-azetidinyl]-2-(2-thienyl)acetic acid (Compound G)

methyl 2-(3-azido-2-oxo-1-azetidinyl)-2-(2-thienyl)acetate to the Compound G methyl 2-[3-(4,5-diphenyl-2-oxo-4-oxazolin-3-yl)-2-oxo-1-azetidinyl]-2-(2-thienyl)acetate to the Compound G methyl 2-(3-phthalimido-2-oxo-1-azetidinyl)-2-(2-furyl)acetate to 2-[3-(2-phenyl-2-hydroxyiminoacetamido)-2-oxo-1-azetidinyl]-2-(2-furyl)acetic acid (Compound H)

[Note: Compounds A and B are disclosed in co-pending U.S. Patent Application Ser. No. 858.375 filed on Dec. 7, 1977 now U.S. Pat. No. 4,207,234; Compounds D, E, F and G are disclosed in copending U.S. Patent Application Ser. No. 730,012 filed on Oct. 6, 1976 now U.S. Pat. No. 4,181,800; and Compound C is disclosed in U.S. Pat. No. 3,923,977 and the Journal of the American Chemical Society, Volume 98, page 3023 (1976)]

Some data of the antimicrobial activities of the 3-acylamino-2-azetidinone compound thus prepared as above are shown for reference in the followings.

| Antibiotics | Microorganisms | MIC value($\mu$g/ml) |
|---|---|---|
| A | Bacillus subtilis | 250 |
| B | Pseudomonas aeruginosa | 4 |
| C | Pseudomonas aeruginosa | 2.5 |
| D | Staphylococcus aureus | 250 |
| E | Staphylococcus aureus | 60 |
| F | Staphylococcus aureus | 250 |
| G | Pseudomonas aeruginosa | 4 |
| H | Pseudomonas aeruginosa | 60 |

Some of the object compounds (III) of this invention and the active 3-acylamino-2-azetidinone compound which are prepared from the object compound of this invention as explained above may be formulated for administration in any convenient way by analogy with other antibiotics.

Thus, the composition of the present invention can be used in the form of pharmaceutical preparation, for example, in solid, semisolid or liquid form, which contains the active object compound (III) of the present invention in admixture with a pharamceutical organic or inorganic carrier, or excipient suitable for external or parenteral applications. The active ingredient may be compounded, for example, with usual carriers into tablets, peletts, capsules, suppositories, solutions, emulsions, aqueous suspensions, and other form suitable for therapeutic administration. The carriers which can be used are glucose, lactose, gum acacia, gelatin, mannitol, starth paste, magnesium trisilicate, talc, corn starch, keratin, colloidal silica, potato starch, urea nad other carriers suitable for use in manufacturing preparations, in solid, semisolid, or liquid form, and in addition auxiliary, stabilizing, thickening and coloring agents and perfumes. The compositions of the present invention can also contain preserving or bacteriostatic agents thereby keeping the active ingredient in the desired preparations stable in activity. The active object compound (III) of the present invention is included in the composition of the present invention in an amount sufficient to produce the desired therapeutic effect upon the bacterially infected process or condition. While the dosage or therapeutically effective quantity of the compound (III) of the present invention varies from and also depends upon the age and condition of each individual patient to be treated, a daily dose of about 0.5–5 g, preferably 1–2 g/day of the active ingredient is generally given.

The following examples are given for the purpose of illustration of the present invention.

Preparation of the starting compound (I)

Preparation 1

A solution of D-2-(2-thienyl)glycine methyl ester hydrochloride (25.0 g.) in water (130 ml.) was mixed with benzene (250 ml.). To this mixture was added dropwise 1 N aqueous sodium hydroxide solution (120 ml.) with stirring under ice-cooling, and then added dropwise 37% aqueous formaldehyde solution (9.9 ml.). After stirring was continued for further 2 hours at the same temperature, the benzene layer was separated and the aqueous layer was extracted with ethyl acetate. The extract and the separated benzene layer were combined, washed with water, dried over magnesium sulfate and evaporagted to dryness under reduced pressure. The residual oil was crystallized from diisopropyl ether to give 1,3,5-tris[D-1-methoxycarbonyl-1-(2-thienyl)methyl]-perhydro-1,3,5-triazine (16.5 g.).

IR $\nu_{max}^{Nujol}$: 1739 cm$^{-1}$.

NMR $\delta$ppm$^{CDCl_3}$: 3.69 (9H, s), 3.78 (6H, s), 4.89 (3H, s), 6.80 to 7.43 (9H, m).

The following compounds were prepared (Preparations 2 to 18) by reacting the corresponding amino acid derivatives with formaldehyde in the substantially same manner as one described in the above Preparation 1.

Preparation 2

1,3,5-Tris(D-α-methoxycarbonyl-3-mesylaminobenzyl)perhydro-1,3,5-triazine.

IR $\nu_{max}^{liq.film}$: 3550 (broad), 3240, 1730 cm$^{-1}$.

NMR $\delta$ppm$^{CDCl_3}$: 3.08 (3H, s), 3.61 (5H, broad s), 4.53 (1H, s), 7.0 to 7.6 (4H, m), 7.71 (1H, broad s).

Preparation 3

1,3,5-Tris[dl-1-methoxycarbonyl-1-(1-naphthyl)methyl]perhydro-1,3,5-triazine, mp 148° to 151° C.

Preparation 4

1,3,5-Tris(dl-1-methoxycarbonyl-2-phenylthioethyl)-perhydro-1,3,5-triazine.

NMR $\delta$ppm$^{CDCl_3}$: 3.10 to 3.90 (15H, m), 3.68 (9H, s), 7.1 to 7.5 (15H, m).

Preparation 5

1,3,5-Tris(4-benzyloxy-α-methoxycarbonylphenethyl)perhydro-1,3,5-triazine, mp 106° to 109° C.

Preparation 6

1,3,5-Tris(dl-erythro-α-methoxycarbonyl-β-methoxyphenethyl)-perhydro-1,3,5-triazine.

Preparation 7

1,3,5-Tris[dl-1-(2-furyl)-1-methoxycarbonylmethyl]-perhydro-1,3,5-triazine.

NMR $\delta$ppm$^{CDCl_3}$: 3.5 to 3.8 (12H, m), 4.74 (3H, s), 6.28 (6H, m), 7.32 (3H, m).

Preparation 8

1,3,5-Tris(methoxycarbonylmethyl)-perhydro-1,3,5-triazine.

IR $\nu_{max}^{liq.film}$: 1740 to 1755 cm$^{-1}$.

NMR $\delta$ppm$^{CDCl_3}$: 3.48 (6H, s), 3.73 (15H, s).

Preparation 9

1,3,5-Tris(ethoxycarbonylmethyl)-perhydro-1,3,5-triazine.

IR $\nu_{max}^{liq.film}$: 1730 to 1750 cm$^{-1}$.

NMR $\delta$ppm$^{CDCl_3}$: 1.25 (9H, t, J=6 Hz), 3.45 (6H, s), 3.73 (6H, s), 4.17 (6H, q, J=6 Hz).

Preparation 10

1,3,5-Tris(benzyloxycarbonylmethyl)-perhydro-1,3,5-triazine.

IR $\nu_{max}^{liq.film}$: 1740 cm$^{-1}$.

NMR $\delta$ppm$^{CDCl_3}$: 3.44 (6H, s), 3.69 (6H, s), 5.10 (6H, s), 7.40 (15H, s).

Preparation 11

1,3,5-Tris(D-α-methoxycarbonylbenzyl)-perhydro-1,3,5-triazine, mp 148° to 155° C.

IR $\nu_{max}^{Nujol}$: 1730 cm$^{-1}$.

NMR $\delta$ppm$^{CDCl_3}$: 3.49 (9H, s), 3.51 (6H, s), 4.50 (1H, s), 7.42 to 6.90 (15H, m).

Preparation 12

1,3,5-Tris(D-4-benzyloxy-α-methoxycarbonylbenzyl)perhydro-1,3,5-triazine, mp 141° to 145° C.

IR $\nu_{max}^{Nujol}$: 1725 cm$^{-1}$.

NMR $\delta$ppm$^{CDCl_3}$: 3.58 (15H, s), 4.50 (3H, s), 5.04 (6H, s), 6.80 (6H, d, J=9 Hz), 7.29 (6H, d, J=9 Hz), 7.40 (15H, s).

Preparation 13

1,3,5-Tris(D-4-benzyloxycarbonyloxy-α-methoxycarbonylbenzyl)-perhydro-1,3,5-triazine.

IR $\nu_{max}^{liq.film}$: 1740, 1710 cm$^{-1}$.

NMR $\delta$ppm$^{CDCl_3}$: 3.50 (15H, s), 4.42 (3H, s), 5.23 (6H, s), 6.99 (6H, d, J=9 Hz), 7.23 (6H, d, J=9 Hz), 7.27 (15H, s).

Preparation 14

1,3,5-Tris(dl-2-methoxycarbonyl-1-phenylethyl)perhydro-1,3,5-triazine, mp 92° to 96° C.
IR $\nu_{max}^{Nujol}$: 1735 cm$^{-1}$.

Preparation 15

1,3,5-Tris(4-methoxycarbonylphenyl)-perhydro-1,3,5-triazine, mp 208° to 209.5° C. (dec.)
IR $\nu_{max}^{Nujol}$: 1710 cm$^{-1}$.

Preparation 16

1,3,5-Tris(D-α-benzyloxycarbonylbenzyl)-perhydro-1,3,5-triazine, mp 118° to 119° C.
IR $\nu_{max}^{Nujol}$: 1730, 1740 (shoulder) cm$^{-1}$.
NMR $\delta ppm^{CDCl_3}$: 3.57 (6H, s), 4.52 (3H, s), 4.95 (6H, s), 6.95 to 7.45 (30H, m).

Preparation 17

1,3,5-Tris(D-α-methoxycarbonyl-3-nitrobenzyl)-perhydro-1,3,5-triazine.
IR $\nu_{max}^{liq.film}$: 1740 cm$^{-1}$.
NMR $\delta ppm^{CDCl_3}$: 3.65 (15H, broad s), 4.65 (3H, s), 7.45 to 8.2 (12H, m).

Preparation 18

1,3,5-Tris(D-α-benzyloxycarbonyl-4-benzyloxybenzyl)-perhydro-1,3,5-triazine, mp 108° to 110° C.
IR $\nu_{max}^{Nujol}$: 1745, 1735, 1720 cm$^{-1}$.
NMR $\delta ppm^{CDCl_3}$: 3.55 (6H, s), 4.47 (3H, s), 4.92 (12H, s), 6.76 (6H, d, J=8 Hz), 7.00 to 7.44 (36H, m).

Preparation 19

A solution of N-tert-butoxycarbonyl-2-(4-hydroxyphenyl) glycine (9.18 g.), phenacyl bromide (6.86 g.) and sodium hydroxide (1.37 g.) in N,N-dimethylformamide (100 ml.) was stirred for 4 hours at ambient temperature. The reaction mixture was poured into water (500 ml.) and extracted three times with every 50 ml. portions of ethyl acetate. The combined extract was washed with water, dried over magnesium sulfate, and evaporated to dryness under reduced pressure to give an oily N-tert-butoxycarbonyl-2-(4-hydroxyphenyl)glycine phenacyl ester (13.19 g.).
IR $\nu_{max}^{liq.film}$: 3400 (broad), 1750, 1710, 1690 cm$^{-1}$.

A mixture of N-tert-butoxycarbonyl-2-(4-hydroxyphenyl)glycine phenacyl ester prepared as above (3.56 g.), phenacyl bromide (1.84 g.) and potassium carbonate (1.28 g.) in an anhydrous acetone (71 ml.) was heated to reflux for 7 hours. The insoluble substances were filtered off and the filtrate was evaporated to dryness under reduced pressure. The residual oil was dissolved in chloroform, washed with water, dried over magnesium sulfate, and evaporated to dryness under reduced pressure. The residue was triturated with diisopropyl ether to give crystalline N-tert-butoxycarbonyl-2-(4-phenacyloxyphenyl)glycine phenacyl ester (4.12 g.), which was recrystallized from ethanol to give the pure material, mp 125° to 126.5° C.

To a solution of N-tert-butoxycarbonyl-2-(4-phenacyloxyphenyl)glycin phenacyl ester (1.0 g.) in ethyl acetate (10 ml.) was added a mixture of hydrobromic acid and acetic acid (2 ml., 4:1 v/v), and then the mixture was stirred for half an hour at ambient temperature. The precipitates were collected by filtration and washed with ethyl acetate to give 2-(4-phenacyloxyphenyl)glycine phenacyl ester hydrobromide (830 mg.), which was recrystallized from a mixture of ethanol, methanol and diethyl ether to give the pure crystals (550 mg.), mp 176° to 177° C.

2-(4-Phenacyloxyphenyl)glycine phenacyl ester hydrobromide (9.5 g.) was reacted with 37% aqueous formaldehyde solution (6 ml.) in the substantially same manner as one described in Preparation 1 to give 1,3,5-tris(4-phenacyloxy-α-phenacyloxycarbonylbenzyl)-perhydro-1,3,5-triazine (7.25 g.), mp 80° to 90° C.
NMR $\delta ppm^{CDCl_3}$: 3.70 (6H, s), 4.65 (3H, s), 5.19 (6H, s), 5.23 (6H, s), 6.86 to 8.04 (42H, m).

Preparation of the objective compound (III)

EXAMPLE 1

To a solution of 2-phthalimidoacetyl chloride (1.34 g.) in dichloromethane (20 ml.) was added dropwise a solution of pyridine (480 mg.) in dichloromethane (2 ml.) in 6 minutes with stirring at −35° to −30° C. and stirring was continued for additional 15 minutes at the same temperature. After cooling down to around −60° to −55° C., to this mixture was added dropwise a mixture of boron trifluoride diethyl etherate (430 mg.) and 1,3,5-tris(D-α-methoxycarbonylbenzyl)-perhydro-1,3,5-triazine (530 mg.) in dichloromethane (10 ml.) in 14 minutes. Stirring was continued for further 3 hours at the same temperature and additional 20 minutes under ice-cooling, and then the reaction mixture was evaporated to dryness under reduced pressure. The residue was treated with a mixture of ethyl acetate (30 ml.) and water (30 ml.) and the insoluble materials were filtered off. The ethyl acetate layer was separated, washed with dilute hydrochloric acid, an aqueous sodium bicarbonate solution and water in turn, dried over magnesium sulfate and evaporated to dryness under reduced pressure. The oily residue (1.34 g.) was subjected to column chromatography on silica gel (15 g.), and eluted with chloroform to give an oily methyl D-2-(2-oxo-3-phthalimido-1-azetidinyl)-2-phenylacetate (850 mg.), which was identified as a mixture of two epimeric isomers (a) and (b) (about 8:1) at 3rd position of the azetidinone ring by NMR spectrometrical determination.

NMR $\delta ppm^{CDCl_3}$:

| due to isomer (a) | due to isomer (b) |
|---|---|
| 3.46 (1H, q, J = 3Hz, 5Hz) | 3.60 (1H, t, J = 5Hz) |
| 3.83 (3H, s) | 3.83 (3H, s) |
| 3.94 (1H, t, J = 5Hz) | 4.10 (1H, q, J = 3Hz, 5Hz) |
| 5.48 (1H, q, J = 3Hz, 5Hz) | 5.34 (1H, q, J = 3Hz, 5Hz) |
| 5.78 (1H, s) | 5.72 (1H, s) |
| 7.38 (5H, s) | 7.36 (5H, s) |
| 7.57 to 7.96 (4H, m) | 7.57 to 7.96 (4H, m) |

EXAMPLE 2

To a cold solution of 1,3,5-Tris(benzyloxycarbonylmethyl)-perhydro-1,3,5-triazine (0.531 g.) in dichloromethane (15 ml.) was added dropwise boron trifluoride diethyl etherate (0.430 g.) at −40° C., and the mixture was stirred for half an hour at the same temperature. On the other hand, to a cold solution of 2-phthalimidoacetyl chloride (1.34 g.) in dichloromethane (15 ml.) was added dropwise a solution of pyridine (0.480 g.) in dichloromethane (5 ml.) with stirring at −35° to −30° C., and stirring was continued for 15 minutes at the same temperature, and then this mixture was further cooled down to −60° C. with stirring. To this latter solution was added dropwise the former mixture prepared above at −60° C. After stirring was continued for an hour at the same temperature, the reaction temperature was raised gradually to −5° to 0° C. for 2 hours with stirring. The reaction mixture was washed with dilute hydrochloric acid, water, a 5% aqueous sodium bicarbonate solution and water in turn, dried over magnesium sulfate and evaporated to dryness under reduced pressure to give an oily residue (1.4 g.). The oil was subjected to column chromatography on silica gel (30 g.), eluted with chloroform and crystallized from diethyl ether to give a mixture of two epimeric isomers at 3rd position of the azetidine ring of benzyl 2-(2-oxo-3-phthalimido-1-azetidinyl)acetate (190 mg.), m.p. 120° to 122° C.

IR $\nu_{max}^{Nujol}$: 1780, 1750, 1730, 1710 cm$^{-1}$.

NMR $\delta$ppm$^{CDCl_3}$: 3.81 to 3.94 (2H, m) 5.08, 5.36 (2H, AB-q, J=18 Hz) 5.19 (2H, s) 5.50, 5.54 (1H, d,d, J=2 Hz, 4 Hz) 7.37 (5H, s) 7.68 to 7.92 (4H, m).

EXAMPLE 3

1,3,5-Tris(D-α-methoxycarbonyl-3-mesylaminobenzyl)-perhydro-1,3,5-triazine (2.53 g.) was dissolved in dichloromethane (30 ml.) and to the solution was added dropwise boron trifluoride diethyl etherate (1.36 g.), and the mixture was left to stand for 15 minutes at ambient temperature. On the other hand, to a solution of 2-phthalimidoacetyl chloride (8.38 g.) in dichloromethane (55 ml.) was added dropwise a mixture of pyridine (1.48 g.) in dichloromethane (8 ml.) in 7 minutes with stirring at −35° to −30° C., and the mixture was further stirred for additional 13 minutes at the same temperature. To this solution, after cooling down to −60° C., was added dropwise the former solution prepared above in 15 minutes. The mixture was stirred for 2 hours at −67° to −60° C., and then for additional half an hour under ice-cooling. The reaction mixture was evaporated to dryness under reduced pressure, and the oily residue was chromatographed on silica gel in the same manner as that of Example 2 to give crystals of methyl D-2-[3-N-mesyl-2-phthalimidoacetamido)phenyl]-2-(2-oxo-3-phthalimido-1-azetidinyl)acetate (0.99 g.), m.p. 127° to 132° C.

IR $\nu_{max}^{Nujol}$: 1780 (shoulder), 1770, 1730, 1720 cm$^{-1}$.

NMR $\delta$ppm$^{CDCl_3}$: 3.57 (3H, s) 3.74 (1H, m) 3.85 (3H, s) 4.03 (1H, t, J=6 Hz) 4.22 (2H, s) 5.54 (1H, d, d, J=6 Hz, 3 Hz) 5.93 (1H, s) 7.60 (12H, m).

EXAMPLE 4

To a cold solution of 2-phthalimidoacetyl chloride (0.67 g.) in dichloromethane (10 ml.) was added dropwise a mixture of pyridine (0.24 g.) and dichloromethane (1 ml.) at −35° to −30° C. in 6 minutes, and the mixture was stirred for 14 minutes at the same temperature. To this solution, after cooling down to −60° C., was added dropwise a mixture of 1,3,5-tris(D-4-benzyloxy-α-methoxycarbonylbenzyl)-perhydro-1,3,5-triazine (0.425 g.) and boron trifluoride diethyl etherate (0.22 g.) in dichloromethane (5 ml.) in 15 minutes, and the mixture was stirred for 2 hours at the same temperature, and then for additional half an hour under ice-cooling. The reaction mixture was evaporated to dryness under reduced pressure, and the residue was treated with a mixture of ethyl acetate (20 ml.) and water (20 ml.). The ethyl acetate layer was separated and the remaining aqueous solution was extracted with ethyl acetate (20 ml.). The ethyl acetate layer and the ethyl acetate extract were combined, washed three times with dilute hydrochloric acid, three times with an aqueous sodium bicarbonate solution, then once with water, dried over magnesium sulfate, and evaporated to dryness under reduced pressure to give an oily residue (0.80 g.). The oil was subjected to column chromatography on silica gel (20 g.), and eluted with chloroform to give an oily mixture of two epimeric isomers (a) and (b) (about 5:1) at the 3rd position of the azetidine ring of methyl D-2-(4-benzyloxyphenyl)-2-(2-oxo-3-phthalimido-1-azetidinyl)acetate (550 mg.).

IR $\nu_{max}^{liq.film}$: 1780, 1760, 1740, 1720 cm$^{-1}$.

NMR $\delta$ppm$^{CDCl_3}$:

| due to isomer (a) | due to isomer (b) |
|---|---|
| 3.42 (1H, d, d, J = 2.5Hz, 6Hz) | 3.66 (1H, t, J = 6Hz) |
| 3.78 (3H, s) | 3.78 (3H, s) |
| 3.90 (1H, t, J = 6Hz) | 4.06 (1H, d, d, J = 2.5Hz, 6Hz) |
| 5.01 (2H, s) | 4.97 (2H, s) |
| 5.06 (1H, d, d, J = 2.5Hz, 6Hz) | 5.32 (1H, d, d, J = 2.5Hz, 6Hz) |
| 5.72 (1H, s) | 5.65 (1H, s) |
| 7.00 (2H, d, J = 9Hz) | 6.98 (2H, d, J = 9Hz) |
| 7.33 (2H, d, J = 9Hz) | 7.35 (2H, d, J = 9Hz) |
| 7.37 (5H, s) | 7.37 (5H, s) |
| 7.70 (4H, m) | 7.70 (4H, m) |

EXAMPLE 5

To a cold solution of 2-phthalimidoacetyl chloride (0.67 g.) in dichloromethane (10 ml.) was added dropwise a solution of pyridine (0.24 g.) in dichloromethane (1 ml.) at −35° to 30° C. in 4 minutes, and the mixture was stirred for 15 minutes at the same temperature. To this solution, after cooling down to −60° C., was added dropwise a mixture 1,3,5-tris(D-4-benzyloxycarbonyloxy-α-methoxycabonylbenzyl)-perhydro-1,3,5-triazine (480 mg.) and boron trifluoride diethyl etherate (0.22 g.) in dichloromethane (5 ml.) in 15 minutes, whereafter the mixture was stirred for additional 3 hours at the same temperature and then for half an hour under ice-cooling. The reaction mixture was evaporated to dryness under reduced pressure, and the residue was treated with a mixture of ethyl acetate (20 ml.) and water (20 ml.). The ethyl acetate layer was separated and the remaining aqueous solution was extracted with ethyl acetate (10 ml.). The extract and the ethyl acetate layer were combined, washed three times with dilute hydrochloric acid, three times with an aqueous sodium bicarbonate solution and once with water, dried over magnesium sulfate, and evaporated to dryness under reduced pressure. The residue, was subjected to column chromatography on silica gel (20 g.) and eluted with chloroform to give an oily mixture of two epimeric isomers (a) and (b) (about 3:1) at 3rd position of the azetidine ring of methyl D-2-(4-benzyloxycarbonyloxyphenyl)-2-(2-oxo-3-phthalimido-1-azetidinyl)acetate (290 mg.).

IR $\nu_{max}^{liq.film}$: 1780, 1760, 1740, 1720 cm$^{-1}$.

NMR $\delta$ppm$^{CDCl_3}$:

| due to isomer (a) | due to isomer (b) |
|---|---|
| 3.49 (1H, d, d, J = 2.5Hz, 6Hz) | 3.75 (1H, t, J = 2.5Hz, 6Hz) |
| 3.94 (1H, t, J = 6Hz) | 3.88 (3H, s) |
| 5.28 (2H, s) | 5.28 (2H, s) |
| 5.50 (1H, d, d, J = 2.5Hz, 6Hz) | 5.35 (1H, d, d, J = 2.5Hz, 6Hz) |
| 5.80 (1H, s) | 5.75 (1H, s) |
| 7.10 to 8.05 (13H, m) | 7.10 to 8.05 (13H, m) |

EXAMPLE 6

2-Phthalimidoacetyl chloride (10.72 g.) was dissolved in dichloromethane (160 ml.) and cooled to −35° to −30° C. To this cold solution was added dropwise a mixture of pyridine (3.84 g.) in dichloromethane (24 ml.) in 7 minutes, and then the mixture was stirred for 15 minutes at the same temperature. To this solution, after cooled down to −60° C., was added dropwise a mixture of 1,3,5-tris(D,L-2-methoxycarbonyl-1-phenylethyl)-perhydro-1,3,5-triazine (4.60 g.) and boron trifluoride diethyl etherate (3.44 g.) in dichloromethane (40 ml.) in 20 minutes, and the mixture was stirred for further 2 hours at the same temperature and then for additional half an hour under ice-cooling. The reaction mixture was evaporated to dryness under reduced pressure, and the residue was treated with a mixture of ethyl acetate (100 ml.) and water (100 ml.). The ethyl acetate layer was separated, washed with dilute hydrochloric acid, an aqueous sodium bicarbonate solution and water in turn, dried over magnesium sulfate, and evaporated to dryness under reduced pressure. The residue was subjected to column chromatography on silica gel (200 g.), and eluted with chloroform to give an oily mixture of two epimeric isomers (a) and (b) (about 1:1) at the 3rd position of the azetidine ring of methyl D,L-3-(2-oxo-3-phthalimido-1-azetidinyl)-3-phenylpropionate (5.06 g.).

This product (100 mg.) was triturated with ethanol to give crystalline mixture of two epimeric isomers (a) and (b) (about 2:1) at the 3rd position of the azetidine ring (60 mg.). m.p. 146° to 153° C.

IR $\nu_{max}^{Nujol}$: 1780, 1745, 1715 cm$^{-1}$.

EXAMPLE 7

To a cold solution of N-benzyloxycarbonylglycyl chloride (710 mg.) in dichloromethane (20 ml.) was added dropwise a solution of pyridine (480 mg.) in dichloromethane (2 ml.) in 4 minutes at −35° to −30° C., and the mixture was stirred for 15 minutes at the same temperature. To this solution was added dropwise a solution of 1,3,5-tris(D-α-methoxycarbonylbenzyl)-perhydro-1,3,5-triazine (530 mg.) a boron trifluoride diethyl etherate (430 mg.) in cichloromethane (10 ml.) in 8 minutes at −65° to −60° C., whereafter the mixture was stirred for 3 hours at the same temperature and then for 15 minutes under ice-cooling. The reaction mixture was evaporated to dryness under reduced pressure and the residue was dissolved in ethyl acetate. The solution was washed with dilute hydrochloric acid, an aqueous sodium bicarbonate solution and water in turn, dried over magnesium sulfate, and then evaporated under reduced pressure. The residue (0.42 g.) was subjected to column chromatography on silica gel (10 g.), eluted with chloroform. The eluate was evaporated under reduced pressure to give an oily mixture of two epimeric isomers at the 3rd position of the azetidine ring of methyl D-2-(3-benzyloxycarbonylamino-2-oxo-1-azetidinyl)-2-phenylacetate (130 mg.).

IR $\nu_{max}^{liq.film}$: 3300, 1740, 1720, 1710 cm$^{-1}$.

EXAMPLE 8

2-Azidoacetyl chloride (720 mg.) was dissolved in dichloromethane (22 ml.). To the solution was added dropwise a solution of pyridine (480 mg.) in dichloromethane (2 ml.) in 3 minutes at −35° to −30° C., and the mixture was stirred for 17 minutes at the same temperature. To this solution was added dropwise a solution 1,3,5-tris(D-α-methoxycarbonylbenzyl)-perhydro-1,3,5-triazine (530 mg.) and boron trifluoride diethyl etherate (430 mg.) in dichloromethane (10 ml.) in 16 minutes at −35° to −30° C. The mixture was stirred for an hour at the same temperature, and then for half an hour under ice-cooling. The reaction mixture was evaporated to dryness under reduced pressure. Diethyl ether (30 ml.) and water (30 ml.) were added to the resultant residue, and the mixture was stirred for a while. The diethyl ether layer was separated, washed with a dilute hydrochloric acid, an aqueous sodium bicarbonate solution and water in turn, dried over magnesium sulfate, and then evaporated under reduced pressure. The residue (0.64 g.) was subjected to column chromatography on silica gel (20 g.) and eluted with chloroform, and the eluate was evaporated under reduced pressure to give an oily mixture of two epimeric isomers (a) and (b) (about 3:1) at the 3rd position of the azetidine ring of methyl D-2-(3-azido-2-oxo-1-azetidinyl)-2-phenylacetate (313 mg.).

IR $\nu_{max}^{liq.film}$: 2080, 1760, 1730 cm$^{-1}$.

NMR $\delta ppm^{CDCl_3}$:

| due to isomer (a) | due to isomer (b) |
|---|---|
| 2.93 (1H, q, J = 2Hz, 6Hz) | 3.26 to 3.76 (2H, m) |
| 3.73 (3H, s) | 3.80 (3H, s) |
| 3.86 (1H, t, J = 6Hz) | 4.50 (1H, q, J = 2Hz, 5Hz) |
| 4.63 (1H, q, J = 2Hz, 6Hz) | 5.60 (1H, s) |
| 5.56 (1H, s) | 7.33 (5H, s) |
| 7.28 (5H, s) | |

EXAMPLE 9

Ethyl chloroformate (650 mg.) was added to a suspension of 2-phthalimidoacetic acid (1.23 g.), triethylamine (606 mg.) and N,N-dimethylbenzylamine (2 drops) in dichloromethane (20 ml.) at −5° C. The mixture was stirred for 25 minutes at the same temperature and then pyridine (480 mg.) was added to the mixture at −60° C. To this solution was added a solution of 1,3,5-tris(D-α-methoxycarbonylbenzyl)-perhydro-1,3,5-triazine (530 mg.) and boron trifluoride diethyl etherate (430 mg.) in dichloromethane (10 ml.) in 10 minutes at the same temperature. The mixture was stirred for 20 minutes at −60° C. and then for additional 3 hours under ice-cooling. The reaction mixture was evaporated to dryness under reduced pressure, and ethyl acetate and water were added to the resultant residue. The insoluble materials were filtered off from the solution and the filtrate was stirred for a while. The ethyl acetate layer was separated, washed with dilute hydrochloric acid, an aqueous sodium bicarbonate solution and water in turn, dried over magnesium sulfate, and evaporated under reduced pressure. The residue (850 mg.) was subject to column chromatography on silica gel (15 g.), eluted with chloroform, and the eluate was evaporated under reduced pressure to give an oily mixture of two epimeric isomers (a) and (b) at the 3rd position of the azetidine ring of methyl D-2-(2-oxo-3-phthalimido-1-azetidinyl)-2-phenylacetate (20 mg.).

NMR $\delta ppm^{CDCl_3}$:

| due to isomer (a) | due to isomer (b) |
|---|---|
| 3.46 (1H, q, J = 3Hz, 5Hz) | 3.60 (1H, t, J = 5Hz) |
| 3.83 (3H, s) | 3.83 (3H, s) |
| 3.94 (1H, t, J = 5Hz) | 4.10 (1H, q, J = 3Hz, 5Hz) |
| 5.48 (1H, q, J = 3Hz, 5Hz) | 5.34 (1H, q, J = 3Hz, 5Hz) |
| 5.78 (1H, s) | 5.72 (1H, s) |
| 7.38 (5H, s) | 7.36 (5H, s) |
| 7.57 to 7.96 (4H, m) | 7.57 to 7.96 (4H, m) |

EXAMPLE 10

2-Phthalimidoacetic acid (1.23 g.) was suspended in dichloromethane (10 ml.), and to the suspension was added dropwise 2,2,2-trifluoroacetic anhydride (1.26 g.), and then the mixture was left to stand for 10 minutes. Triethylamine (600 mg.) was added to the solution and the mixture was stirred for 20 minutes at ambient temperature. To this solution were added dropwise pyridine and a solution of 1,3,5-tris(D-α-methoxycarbonylbenzyl)-perhydro-1,3,5-triazine (530 mg.) and boron trifluoride diethyl ethalate (430 mg.) in dichloromethane (10 ml.) in 10 minutes at −60° C. The mixture was stirred for 1.5 hours at the same temperature and for additional half an hour at 5° C. The reaction mixture was evaporated to dryness under reduced pressure, and ethyl acetate (50 ml.) and water (30 ml.) were added to the resultant residue. The insoluble materials were filtered off, and the filtrate was stirred for a while. The ethyl acetate layer was separated, washed with dilute hydrochloric acid, an aqueous sodium bicarbonate solution and water in turn, dried over magnesium sulfate, and then evaporated to dryness under reduced pressure. The residue (700 mg.) was subjected to column chromatography on silica gel (30 g.), and eluted with chloroform. The eluate was evaporated under reduced pressure to give an oily mixture of two epimeric isomers (a) and (b) at the 3rd position of the azetidine ring of methyl D-2-(2-oxo-3-phthalimido-1-azetidinyl)-2-phenylacetate (80 mg.).

NMR δppm$^{CDCl_3}$ :

| due to isomer (a) | due to isomer (b) |
|---|---|
| 3.46 (1H, q, J = 3Hz, 5Hz) | 3.60 (1H, t, J = 5Hz) |
| 3.83 (3H, s) | 3.83 (3H, s) |
| 3.94 (1H, t, J = 5Hz) | 4.10 (1H, q, J = 3Hz, 5Hz) |
| 5.48 (1H, q, J = 3Hz, 5Hz) | 5.34 (1H, q, J = 3Hz, 5Hz) |
| 5.78 (1H, s) | 5.72 (1H, s) |
| 7.38 (5H, s) | 7.36 (5H, s) |
| 7.87 to 7.96 (4H, m) | 7.57 to 7.96 (4H, m) |

EXAMPLE 11

2-Phthalimidoacetyl chloride (5.38 g.) was dissolved in dichloromethane (80 ml.), and to the solution was added dropwise a solution of pyridine (1.92 g.) in dichloromethane (8 ml.) in 16 minutes at −35° to −30° C. The mixture was stirred for 4 minutes at the same temperature. A solution of 1,3,5-tris-(D-α-benzyloxycarbonylbenzyl)-perhydro-1,3,5-triazine (3.04 g.) and boron trifluoride diethyl etherate (1.72 g.) in dichloromethane (40 ml.) was added dropwise to the solution prepared above in 40 minutes at −60° C. The mixture was stirred for 2 hours at the same temperature and then for half an hour under ice-cooling. The reaction mixture was evaporated to dryness under reduced pressure, and water and ethyl acetate were added to the resultant residue. Insoluble materials in the mixture were filtered off. The ethyl acetate layer was separated from the filtrate, washed with dilute hydrochloric acid and a saturated aqueous sodium chloride solution, dried over magnesium sulfate, and then evaporated under reduced pressure. The residue (7.55 g.) was subjected to column chromatography on silica gel (250 g.), eluted with chloroform and the eluate was evaporated under reduced pressure to give an oily mixture of two epimeric isomers (a) and (b) (about 3:1) at the 3rd position of the azetidine ring of benzyl D-2-(2-oxo-3-phthalimido-1-azetidinyl)-2-phenylacetate (3.46 g.).

NMR δppm$^{CDCl_3}$ :

| due to isomer (a) | due to isomer (b) |
|---|---|
| 3.42 (1H, d, d, J = 3Hz, 6Hz) | 3.59 (1H, t, J = 6Hz) |
| 3.93 (1H, t, J = 6Hz) | 4.11 (1H, d, d, J = 3Hz, 6Hz) |
| 5.27 (2H, s) | 5.28 (2H, s) |
| 5.53 (1H, d, d, J = 3Hz, 6Hz) | 5.32 (1H, m) |
| 5.90 (1H, s) | 5.82 (1H, s) |
| 7.38 (5H, s) | 7.25 to 7.45 (10H, m) |
| 7.44 (5H, s) | 7.65 to 7.90 (4H, m) |
| 7.7 to 7.9 (4H, m) | |

EXAMPLE 12

2-(2-Oxo-4,5-diphenyl-4-oxazolin-3-yl)acetyl chloride (1.88 g.) was dissolved in dichloromethane (20 ml.), and to the solution was added dropwise a solution of pyridine (480 mg.) in dichloromethane (2 ml.) in 4 minutes at −35° to −30° C. The mixture was stirred for 15 minutes at the same temperature. To this solution was added a solution of 1,3,5-tris(D-α-methoxycarbonylbenzyl)-perhydro-1,3,5-triazine (530 mg.) and boron trifluoride diethyl etherate (430 mg.) in dichloromethane (10 ml.) in 15 minutes at −60° C. The mixture was stirred for 2 hours at the same temperature and then for an hour under ice-cooling. The reaction mixture was evaporated to dryness under reduced pressure. To the residue was added a mixture of ethyl acetate (30 ml.) and water, and the mixture was stirred for a while. The ethyl acetate layer was separated, washed twice with 1% hydrochloric acid, twice with 1% aqueous sodium bicarbonate and once with water, dried over magnesium sulfate, and then evaporated to dryness under reduced pressure. The residue was subjected to column chromatography on silica gel (25 g.), eluted with chloroform. The eluate was evaporated under reduced pressure to give an amorphous mixture of two epimeric isomers (a) and (b) (about 5 to 4:1) at the 3rd position of the azetidine ring of methyl D-2-[2-oxo-3-(2-oxo-4,5-diphenyl-4-oxazolin-3-yl)-1-azetidinyl]-2-phenylacetate (1.09 g.).

IR $\nu_{max}^{liq.film}$: 1760 cm$^{-1}$.

NMR δppm$^{CDCl_3}$ :

| due to isomer (a) | due to isomer (b) |
|---|---|
| 3.47 (1H, d, d, J = 2.5Hz, 6Hz) | 3.48 (1H, t, J = 6Hz) |
| 3.72 (3H, s) | 3.72 (3H, s) |
| 3.76 (1H, t, J = 6Hz) | 4.11 (1H, d, d, J = 2.5Hz, 6Hz) |
| 4.91 (1H, d, d, J = 2.5Hz, 6Hz) | 4.78 (1H, d, d, J = 2.5Hz, 6Hz) |
| 5.56 (1H, s) | 5.50 (1H, s) |
| 6.88 to 7.60 (15H, m) | 6.88 to 7.60 (15H, m) |

EXAMPLE 13

A mixture of two epimeric isomers (a) and (b) (about 3:2) of methyl D,L-2-(2-oxo-3-phthalimido-1-azetidinyl)-3-phenylthiopropionate (1.22 g.) was obtained by reacting 1,3,5-tris(D,L-1-methoxycarbonyl-2-phenylthioethyl)-perhydro-1,3,5-triazine (5.40 g.) with 2-phthalimidoacetyl chloride (11.56 g.) in the presence of boron trifluoride diethyl etherate (7.32 g.) and pyridine (8.18 g.) in the substantially similar manner to that of Example 10.

IR $\nu_{max}^{Nujol}$: 1785, 1770, 1735, 1715 cm$^{-1}$.

NMR δppm$^{CDCl_3}$ :

| due to isomer (a) | due to isomer (b) |
|---|---|
| 3.1 to 3.9 (4H, m) | 3.1 to 3.9 (4H, m) |
| 3.76 (3H, s) | 3.76 (3H, s) |
| 4.64 (1H, d, d, J = 8.5, 5Hz) | 4.64 (1H, d, d, J = 8.5, 5Hz) |
| 5.20 (1H, d, d, J = 6, 3Hz) | 5.40 (1H, t, J = 6Hz) |
| 7.30 (5H, m) | 7.30 (5H, m) |

| 7.70 (4H, m) | 7.70 (4H, m) |

EXAMPLE 14

A mixture of two epimeric isomers of methyl D,L-2-(1-naphthyl)-2-(2-oxo-3-phthalimido-1-azetidinyl)acetate (3.13 g.) was obtained by reacting 1,3,5-tris[D,L-1-methoxycarbonyl-1-(1-naphthyl)methyl]-perhydro-1,3,5-triazine (4.00 g.) with 2-phthalimidoacetyl chloride (2.50 g.) in the presence of boron trifluoride diethyl etherate (2.50 g.) and pyridine (2.78 g.) in the substantially similar manner to that of Example 10. Thus obtained compound was pulverized with diethyl ether, and the resultant powder (2.10 g.) was recrystallized from ethanol to give one of two isomers of the object compound. m.p. 200.5° to 201.5° C.

IR $\nu_{max}^{Nujol}$: 1724, 1740, 1750 1782 cm$^{-1}$.

NMR $\delta ppm^{CDCl_3}$: 3.16 (1H, d,d, J=6, 3 Hz) 3.80 (3H, s) 3.89 (1H, t, J=6 Hz) 5.50 (1H, d,d, J=6, 3 Hz) 6.45 (1H, s) 7.3 to 8.3 (7H, m).

EXAMPLE 15

A mixture of two epimeric isomers (a) and (b) (about 3:2) of methyl D,L-erythro-3-methoxy-3-phenyl-2-(2-oxo-3-phthalimido-1-azetidinyl)propionate (6.73 g.) was obtained by reacting 1,3,5-tris(D,L-erythro-α-methoxycarbonyl-β-methoxyphenethyl)-perhydro-1,3,5-triazine (6.66 g.) with 2-phthalimidoacetyl chloride (13.45 g.) in the presence of boron trifluoride diethyl etherate (4.25 g.) and pyridine (4.74 g.) in the substantially similar manner to that of Example 10.

Thus obtained compound was pulverized with diethyl ether to give the isomer (a) (3.05 g.) m.p. 150° to 155° C.

IR $\nu_{max}^{Nujol}$: 1785 (shoulder), 1760, 1735, 1715 cm$^{-1}$.

| NMR $\delta ppm^{CDCl_3}$: | |
|---|---|
| due to isomer (a) | due to isomer (b) |
| 3.24 (3H, s) | 3.36 (3H, s) |
| 3.86 (3H, s) | 3.68 (3H, s) |
| 4.56 (1H, d, J = 8Hz) | 4.71 (1H, d, J = 6Hz) |
| 4.84 (1H, d, J = 8Hz) | 4.95 (1H, d, J = 6Hz) |
| 5.08 (1H, d, d, J = 3, 6Hz) | 5.38 (1H, d, d, J = 6, 4Hz) |
| 7.37 (5H, s) | 7.40 (5H, s) |
| 7.6 to 7.8 (4H, m) | 7.60 to 7.9 (4H, m) |

EXAMPLE 16

A mixture of two epimeric isomers of methyl D,L-3-(4-benzyloxyphenyl)-2-(2-oxo-3-phthalimido-1-azetidinyl) propionate (4.95 g.) was obtained by reacting 1,3,5-tris(D,L-α-methoxycarbonyl-4-benzyloxyphenethyl)-perhydro-1,3,5-triazine (9.0 g.) and 2-phthalimidoacetyl chloride (13.5 g.) in the presence of boron trifluoride diethyl etherate (4.3 g.) and pyridine (4.7 g.) in the substantially similar manner to that of Example 10.

IR $\nu_{max}^{Nujol}$: 1780, 1760, 1738, 1705 cm$^{-1}$.

EXAMPLE 17

A solution of pyridine (480 mg.) in dichloromethane (2 ml.) was added dropwise to a solution of 2-phthalimidoacetyl chloride (1.34 g.) in dichloromethane (20 ml.) in 15 minutes at −35° to −30° C. To the solution was added dropwise a solution of 1,3,5-tris[D-1-(2-thienyl)-1-methoxycarbonylmethyl]-perhydro-1,3,5-triazine (550 mg.) and boron trifluoride diethyl etherate (430 mg.) in dichloromethane (10 ml.) in 15 minutes at −60° C. The mixture was stirred for 2 hours at the same temperature and then for half an hour under ice-cooling. The reaction mixture was evaporated to dryness under reduced pressure. Ethyl acetate (30 ml.) and water (30 ml.) were poured into the resultant residue, and the insoluble materials were filtered off. The ethyl acetate layer was separated from the filtrate, and the remaining aqueous layer was extracted with ethyl acetate. The extract was combined with the ethyl acetate layer, washed three times with dilute hydrochloric acid, three times with aqueous sodium bicarbonate solution and once with water, dried over magnesium sulfate, and then evaporated under reduced pressure. The residue was subjected to column chromatography on silica gel (20 g.), and eluted with chloroform. The eluate was evaporated under reduced pressure to give an oily mixture of two isomers of methyl D-2-(2-oxo-3-phthalimido-1-azetidinyl)-2-(2-thienyl)acetate (720 mg.). Thus obtained compound was recrystallized from ethanol to give one of two epimeric isomers (300 mg.). m.p. 167° to 170° C.

EXAMPLE 18

A mixture of two epimeric isomers (a) and (b) (about 1:1) of methyl D-2-(3-azido-2-oxo-1-azetidinyl)-2-(2-thienyl)acetate (3.41 g.) was obtained by reacting 1,3,5-tris[D-1-methoxycarbonyl-1-(2-thienyl)methyl]-perhydro-1,3,5-triazine (7.8 g.) with 2-azidoacetyl chloride (10.1 g.) in the presence of boron trifluoride diethyl etherate (6.10 g.) and pyridine (6.73 g.) in the substantially similar manner to that of Example 17.

| NMR $\delta ppm^{CDCl_3}$: | |
|---|---|
| due to isomer (a) | due to isomer (b) |
| 3.17 (1H, d, d, J = 2.5, 6Hz) | 3.60 (2H, m) |
| 3.80 (3H, s) | 3.82 (3H, s) |
| 3.95 (1H, t, J = 6Hz) | 4.53 (1H, d, d, J = 2.5, 6Hz) |
| 4.70 (1H, d, d, J = 2.5, 6Hz) | 5.87 (1H, s) |
| 5.88 (1H, s) | 7.05 (2H, m) |
| 7.05 (2H, m) | 7.26 (1H, m) |
| 7.26 (1H, m) | |

EXAMPLE 19

A mixture of two epimeric isomers (a) and (b) (about 2:1) of methyl D-2-[2-oxo-3-(2-oxo-4,5-diphenyl-4-oxazolin-3-yl)-1-azetidinyl]-2-(2-thienyl)acetate (1.86 g.) was obtained by reacting 1,3,5-tris[D-1-methoxycarbonyl-1-(2-thienyl)methyl]-perhydro-1,3,5-triazine (1.10 g.) with 2-(2-oxo-4,5-diphenyl-4-oxazolin-3-yl)acetyl chloride (3.96 g.) in the presence of boron trifluoride diethyl etherate (860 mg.) and pyridine (960 mg.) in the substantially similar manner to that of Example 17.

| NMR $\delta ppm^{CDCl_3}$: | |
|---|---|
| due to isomer (a) | due to isomer (b) |
| 3.67 (1H, d, d, J = 2.5, 6Hz) | 3.60 (1H, t, J = 6Hz) |
| 3.76 (3H, s) | 3.80 (3H, s) |
| 3.84 (1H, t, J = 6Hz) | 4.08 (1H, d, d, J = 2.5, 6Hz) |
| 4.92 (1H, d, d, J = 2.5, 6Hz) | 4.80 (1H, d, d, J = 2.5, 6Hz) |
| 5.82 (1H, s) | 5.78 (1H, s) |
| 6.88 to 7.62 (13H, m) | 6.88 to 7.62 (13H, m) |

EXAMPLE 20

A mixture of two epimeric isomers (a) and (b) (about 2:1) of phenacyl D-2-(2-oxo-3-phthalimido-1-azetidinyl)-2-(4-phenacyloxyphenyl)acetate (830 mg.) was obtained by reacting 1,3,5-tris(α-phenacyloxycarbonyl-4-phenacyloxybenzyl)-perhydro-1,3,5-triazine (1.24 g.) with 2-phthalimidoacetyl chloride (1.34 g.) in the presence of boron trifluoride diethyl etherate (1.55 g.) and pyridine (1.11 g.) in a similar manner to that of Example 10.

IR $\nu_{max}^{liq.film}$: 1780 (sh), 1760, 1720, 1700, 1680 (sh) cm$^{-1}$.

| NMR δppm$^{CDCl_3}$: | |
|---|---|
| due to isomer (a) | due to isomer (b) |
| 3.43 (1H, d, d, J = 3Hz, 5Hz) | 3.55 (1H, t, J = 5Hz) |
| 3.82 (1H, t, J = 5Hz) | 4.06 (1H, d, d, J = 3Hz, 5Hz) |
| 5.30 to 5.54 (5H, m) | 5.30 to 5.54 (5H, m) |

EXAMPLE 21

A mixture of two epimeric isomers (a) and (b) (about 4:1) of methyl dl-2-(2-furyl)-2-(2-oxo-3-phthalimido-1-azetidinyl)acetate (1.44 g. m.p. 176° to 178° C.) was obtained by reacting 1,3,5-tris(α-methoxycarbonyl-2-furfuryl)-perhydro-1,3,5-triazine (4.05 g.) with 2-phthalimidoacetyl chloride (10.8 g.) in the presence of boron trifluoride diethyl etherate (3.44 g.) and pyridine (3.81 g.) in the substantially similar manner to that of Example 10.

IR $\nu_{max}^{Nujol}$: 1770 (sh), 1760, 1730, 1710 cm$^{-1}$.

| NMR δppm$^{CDCl_3}$: |
|---|
| due to isomer (a) |
| 3.64 (1H, d, d, J = 3Hz, 6Hz) |
| 3.80 (3H, s) |
| 4.02 (1H, t, J = 6Hz) |
| 5.52 (1H, d, d, J = 3Hz, 6Hz) |
| 5.84 (1H, s) |
| 6.44 (1H, m) |
| 6.56 (1H, d, J = 4Hz) |
| 7.47 (1H, d, J = 3Hz) |
| 7.77 (4H, m) |

EXAMPLE 22

A mixture of two epimeric isomers (a) and (b) of benzyl D-2-(3-azido-2-oxo-1-azetidinyl)-2-(4-benzyloxyphenyl)acetate (1.10 g.) was obtained by reacting 1,3,5-tris(α-benzyloxycarbonyl-4-benzyloxybenzyl)-perhydro-1,3,5-triazine (1.35 g.) with 2-azidoacetyl chloride (890 mg.) in the presence of boron trifluoride diethyl etherate (800 mg.) and pyridine (750 mg.) in a similar manner to that of Example 10.

IR $\nu_{max}^{liq.film}$: 2100, 1765, 1735 cm$^{-1}$.

| NMR δppm$^{CDCl_3}$: | |
|---|---|
| due to isomer (a) | due to isomer (b) |
| 2.94 (1H, d, d, J = 2Hz, 5Hz) | 3.35 (1H, t, J = 5Hz) |
| 3.84 (1H, t, J = 5Hz) | 3.56 (1H, d, d, J = 2Hz, 5Hz) |
| 4.62 (1H, d, d, J = 2Hz, 5Hz) | 4.46 (1H, d, d, J = 2Hz, 5Hz) |
| 5.03 (2H, s) | 5.03 (2H, s) |
| 5.13 (2H, s) | 5.18 (2H, s) |
| 5.61 (1H, s) | 5.58 (1H, s) |
| 7.09 (4H, AB-q, J = 8Hz) | 7.09 (4H, AB-q, J = 8Hz) |
| 7.12 to 7.56 (10H, m) | 7.12 to 7.56 (10H, m) |

EXAMPLE 23

A mixture of two epimeric isomers (a) and (b) (about 5:2) of benzyl dl-2-(3-benzyloxy-2-oxo-1-azetidinyl)-2-phenylacetate (530 mg.) was obtained by reacting 1,3,5-tris (D-α-benzyloxycarbonylbenzyl)-perhydro-1,3,5-triazine (1.52 g.) with benzyloxyacetyl chloride (2.21 g.) in the presence of boron trifluoride diethyl etherate (860 mg.) and pyridine (960 mg.) in a similar manner to that of Example 10.

IR $\nu_{max}^{liq.film}$: 1760, 1740 cm$^{-1}$.

| NMR δppm$^{CDCl_3}$: | |
|---|---|
| due to isomer (a) | due to isomer (b) |
| 3.18 (1H, d, d, J = 4Hz, 5Hz) | 3.52 (1H, d, d, J = 4Hz, 5Hz) |
| 4.02 (1H, d, d, J = 5Hz, 6Hz) | 3.78 (1H, d, d, J = 2Hz, 4Hz) |
| 5.17 (4H, s) | 5.12 (1H, d, d, J = 2Hz, 6Hz) |
| 5.27 (1H, d, d, J = 2Hz, 5Hz) | 5.17 (4H, s) |
| 5.75 (1H, s) | 5.72 (1H, s) |
| 6.8 to 7.4 (15H, m) | 6.8 to 7.4 (15H, m) |

EXAMPLE 24

A mixture of two epimeric isomers (a) and (b) (about 1:1) of methyl D-2-(3-phenoxy-2-oxo-1-azetidinyl)-2-phenylacetate (730 mg.) was obtained by reacting 1,3,5-tris (α-methoxycarbonylbenzyl)-perhydro-1,3,5-triazine (1.06 g.) with phenoxyacetyl chloride (2.05 g.) in the presence of boron trifluoride diethyl etherate (685 mg.) and pyridine (950 mg.) in a substantially similar manner to that of Example 10.

IR $\nu_{max}^{liq.film}$: 1790, 1740 cm$^{-1}$.

| NMR δppm$^{CDCl_3}$: | |
|---|---|
| due to isomer (a) | due to isomer (b) |
| 3.15 (1H, d, d, J = 2Hz, 6Hz) | 3.52 (1H, d, d, J = 5Hz, 6Hz) |
| 3.70 (3H, s) | 3.70 (3H, s) |
| 5.28 (1H, d, d, J = 2Hz, 5Hz) | 5.06 (1H, d, d, J = 2Hz, 5Hz) |
| 5.67 (1H, s) | 5.63 (1H, s) |
| 6.8 to 7.4 (10H, m) | 6.8 to 7.4 (10H, m) |

EXAMPLE 25

A mixture of two epimeric isomers (a) and (b) (about 1:1) of methyl D-2-(3-chloro-2-oxo-1-azetidinyl)-2-phenylacetate (200 mg.) was obtained by reacting 1,3,5-tris(D-α-methoxycarbonylbenzyl)-perhydro-1,3,5-triazine (1.06 g.) with chloroacetyl chloride (1.36 g.) in the presence of boron trifluoride diethyl etherate (685 mg.) and pyridine (950 mg.) in a substantially similar manner to that of Example 10.

IR $\nu_{max}^{liq.film}$: 1770 (broad), 1740 cm$^{-1}$.

| NMR δppm$^{CDCl_3}$: | |
|---|---|
| due to isomer (a) | due to isomer (b) |
| 3.14 (1H, d, d, J = 2Hz, 6Hz) | 3.60 (1H, t, J = 6Hz) |
| 3.75 (3H, s) | 3.78 (3H, s) |
| 4.81 (1H, d, d, J = 2Hz, 5Hz) | 4.77 (1H, d, d, J = 2Hz, 6Hz) |
| 5.64 (1H, s) | 5.61 (1H, s) |
| 7.2 to 7.5 (5H, m) | 7.2 to 7.5 (5H, m) |

EXAMPLE 26

A mixture of two epimeric isomers of methyl D-2-(3-diethylphosphorylamino-2-oxo-1-azetidinyl)-2-phenylacetate (60 mg.) was obtained by reacting 1,3,5-tris (α-methoxy carbonylbenzyl)-perhydro-1,3,5-triazine (530 mg.) with diethylphosphorylaminoacetyl chloride prepared from the corresponding acid (1.27 g.) in the presence of boron trifluoride diethyl etherate (430 mg.) and pyridine (480 mg.) in a substantially similar manner to that of Example 10.

IR $\nu_{max}^{liq.film}$: 3450, 1750, 1710, 1270 cm$^{-1}$.

NMR $\delta$ppm$^{CDCl_3}$: 1.28 (3H, t, J=7 Hz); 3.75 (3H, s); 3.78 to 4.31 (6H, m); 4.98 (1H, m); 5.99 (1H, s); 7.32 (5H, m).

EXAMPLE 27

A mixture of two epimeric isomers (a) and (b) of Benzyl D-2-(4-benzyloxyphenyl)-2-(2-oxo-3-phthalimido-1-azetidinyl)acetate (6.68 g.) was obtained by reacting 1,3,5-tris(α-benzyloxycarbonyl-4-benzyloxybenzyl)-perhydro-1,3,5-triazine (5.40 g.) with 2-phthalimidoacetyl chloride (6.70 g.) in the presence of boron trifluoride diethyl etherate (2.15 g.) and pyridine (2.40 g.) in a substantially similar manner to that of Example 10. Thus obtained mixthur was recrystallized from a mixture of diethyl ether and ethanol, and then from ethanol to give the isomer (a). m.p. 127° to 128° C. The former mother liquor was concentrated under reduced pressure, and the residue was recrystallized from a mixture of a slight amount of ethanol and diethyl ether, and then from ethanol to give the isomer (b). m.p. 105° to 107.5° C.

Isomer (a)

NMR $\delta$ppm$^{CDCl_3}$: 3.40 (1H, d,d, J=4.5 Hz, 2.5 Hz); 3.89 (1H, t, J=4.5 Hz); 5.02 (2H, s); 5.21 (2H, s); 5.47 (1H, d,d, J=4.5 Hz, 2.5 Hz); 5.79 (1H, s); 6.92 to 7.52 (14H, m); 7.56 to 7.90 (4H, m).

Isomer (b)

NMR $\delta$ppm$^{CDCl_3}$: 3.55 (1H, t, J=4.5 Hz); 4.05 (1H, d,d, J=4.5 Hz, 2.5 Hz); 5.02 (2H, s); 5.24 (2H, s); 5.31 (1H, d,d, J=4.5 Hz, 2.5 Hz); 5.70 (1H, s); 6.89 to 7.50 (14H, m); 7.60 to 7.94 (4H, m).

EXAMPLE 28

A mixture of two epimeric isomers (a) and (b) of Benzyl D-2-(4-bezyloxycarbonyloxyphenyl)-2-(2-oxo-3-phthalimido-1-azetidinyl)acetate (1.41 g.) was obtained by reacting 1,3,5-tris (α-benzyloxycarbonyl-4-benzyloxycarbonyloxybenzyl)-perhydro-1,3,5-triazine (1.21 g.) with 2-phthalimidoacetyl chloride (1.34 g.) in the presence of boron trifluoride diethyl etherate (850 mg.) and pyridine (720 mg.) in a substantially similar manner to that of Example 10.

IR $\nu_{max}^{liq.film}$: 1780 (sh), 1765, 1750 (sh), 1720 cm$^{-1}$.

NMR $\delta$ppm$^{CDCl_3}$:

| due to isomer (a) | due to isomer (b) |
|---|---|
| 3.41 (1H, d, d, J = 2.5Hz, 5.5Hz) | 3.63 (1H, t, J = 5.5Hz) |
| 3.89 (1H, t, J = 5.5Hz) | 4.13 (1H, d, d, J = 2.5Hz, 5.5Hz) |
| 5.23 (2H, s) | 5.31 (4H, s) |
| 5.24 (2H, s) | 5.42 (1H, d, d, J = 2.5Hz, 5.5Hz) |
| 5.48 (1H, d, d, J = 2.5 Hz, 5.5Hz) | 5.90 (1H, s) |
| 5.86 (1H, s) | 7.06 to 7.52 (14H, m) |
| 7.06 to 7.52 (14H, m) | 7.72 (4H, m) |
| 7.72 (4H, m) | |

We claim:

1. A process for preparing an azetidinone of the formula:

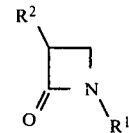

which comprises reacting a C-unsubstituted methyleneamine of the formula:

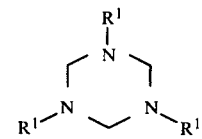

with substituted acetic acid of the formula, $R^2$-CH$_2$COOH, its acid halide or its acid anhydride with alkyl carbonic acid or an aliphatic carboxy acid, in the presence of boron trihalide and an organic base, wherein $R^1$ is C$_1$–C$_2$ alkyl bearing a carboxy group or its ester at the first position of the alkyl moiety; phenyl- or naphthyl-(C$_1$–C$_2$)alkyl bearing a carboxy group or its ester at α-position of the alkyl moiety, in which the phenyl moiety may be substituted with a protected hydroxy group; or 5-membered aromatic monocyclic heterocyclic-(C$_1$–C$_2$)alkyl bearing a carboxy group or its ester at the first position of the alkyl moiety, in which said heterocyclic moiety contains one hetero atom selected from oxygen and sulfur atoms, and $R^2$ is azido or a protected amino group.

2. A process according to claim 1 wherein said organic base is pyridine.

3. A process according to claim 1 wherein $R^2$ is a protected amino group.

4. A process according to claim 1 wherein $R^2$ is acylamino or aralkylamino.

* * * * *